(12) United States Patent
Dhuppad et al.

(10) Patent No.: US 11,679,210 B2
(45) Date of Patent: Jun. 20, 2023

(54) DISPENSING DEVICE AND PHARMACEUTICAL COMPOSITION FOR THE TREATMENT OF RHINITIS

(71) Applicant: Glenmark Specialty S.A., La Chaux-de-Fonds (CH)

(72) Inventors: Ulhas R. Dhuppad, Maharashtra (IN); Ashok Katkurwar, Maharashtra (IN); Yashwant Gupta, Maharashtra (IN); Rajesh Ankam, Maharashtra (IN); Chandrakant Dhatrak, Maharashtra (IN); Neelima Khairatkar-Joshi, Maharashtra (IN); Abhay Kulkarni, Maharashtra (IN); Dinesh Pradeep Wale, Maharashtra (IN); Vikram Mansingh Bhosale, Maharshtra (IN); Piyush Agarwal, Maharashtra (IN); Patrick Keohane, London (GB); Sudeesh K. Tantry, Jamison, PA (US); Chad Oh, San Francisco, CA (US)

(73) Assignee: GLENMARK SPECIALTY S.A., La Chaux-de-Fonds (CH)

( * ) Notice: Subject to any disclaimer, the term of this patent is extended or adjusted under 35 U.S.C. 154(b) by 67 days.

(21) Appl. No.: 16/303,609

(22) PCT Filed: Jun. 28, 2018

(86) PCT No.: PCT/US2018/040098
§ 371 (c)(1),
(2) Date: Nov. 20, 2018

(87) PCT Pub. No.: WO2019/006173
PCT Pub. Date: Jan. 3, 2019

(65) Prior Publication Data
US 2021/0220574 A1  Jul. 22, 2021

(30) Foreign Application Priority Data

Apr. 16, 2018  (IN) .............................. 201821014426

(51) Int. Cl.
*A61M 11/00* (2006.01)
*A61K 31/58* (2006.01)
(Continued)

(52) U.S. Cl.
CPC ......... *A61M 11/007* (2014.02); *A61K 9/0043* (2013.01); *A61K 31/335* (2013.01);
(Continued)

(58) Field of Classification Search
CPC .. A61M 15/0065; A61M 15/08; A61M 31/00;
A61M 2210/0618;
(Continued)

(56) References Cited

U.S. PATENT DOCUMENTS 2,564,400 A  10/1949 Hall
4,871,865 A  10/1989 Lever, Jr. et al.
(Continued)

FOREIGN PATENT DOCUMENTS

CN  1787879 A  6/2006
CN  101678182 A  3/2010
(Continued)

OTHER PUBLICATIONS

Supplementary European Search Report issued in EP18823894 dated Apr. 8, 2019.
(Continued)

*Primary Examiner* — Elliot S Ruddie
(74) *Attorney, Agent, or Firm* — Blank Rome LLP

(57) ABSTRACT

A nasal dispensing device and pharmaceutical composition includes a container; a dispenser head having at least a pump, a dispensing channel, and a dispensing orifice; a dip
(Continued)

tube; and a pharmaceutical composition comprising mometasone, an ester thereof (e.g., mometasone furoate), or a salt thereof and olopatadine or its salt (e.g., olopatadine hydrochloride). The container can have a conically shaped internal bottom, angled downwardly toward a center, and a further angularly deepened well, centrally located, with the dip tube extending into the well. An optional cap is provided that includes a sealing sleeve communicating in a seal tight manner with a perimeter of a lateral wall of the dispenser head.

16 Claims, 3 Drawing Sheets

(51) Int. Cl.
| | |
|---|---|
| A61K 31/335 | (2006.01) |
| A61K 9/00 | (2006.01) |
| A61K 47/38 | (2006.01) |
| A61K 47/02 | (2006.01) |
| A61K 47/18 | (2017.01) |
| A61K 47/24 | (2006.01) |
| A61K 47/26 | (2006.01) |
| A61P 37/08 | (2006.01) |
| A61M 15/00 | (2006.01) |
| A61M 15/08 | (2006.01) |
| A61M 31/00 | (2006.01) |
| B05B 15/30 | (2018.01) |
| A61K 47/36 | (2006.01) |
| B05B 11/00 | (2023.01) |

(52) U.S. Cl.
CPC .............. A61K 31/58 (2013.01); A61K 47/02 (2013.01); A61K 47/183 (2013.01); A61K 47/186 (2013.01); A61K 47/24 (2013.01); A61K 47/26 (2013.01); A61K 47/36 (2013.01); A61K 47/38 (2013.01); A61M 15/0065 (2013.01); A61M 15/08 (2013.01); A61M 31/00 (2013.01); A61P 37/08 (2018.01); B05B 15/30 (2018.02); A61M 2210/0618 (2013.01); B05B 11/0037 (2013.01)

(58) Field of Classification Search
CPC .. A61M 2202/0468; A61M 2205/0238; A61M 11/006–008; A61K 9/0043; A61K 31/335; A61K 31/58; A61K 47/02; A61K 47/183; A61K 47/186; A61K 47/24; A61K 47/26; A61K 47/38; A61K 9/10; A61K 47/36; A61P 37/08; A61P 11/02; A61P 27/14; B05B 15/30; B05B 11/0037
See application file for complete search history.

(56) References Cited

U.S. PATENT DOCUMENTS

| | | | |
|---|---|---|---|
| 4,923,892 A | 5/1990 | Lever, Jr. et al. | |
| 5,062,549 A * | 11/1991 | Smith | B05B 15/30 222/382 |
| 5,837,699 A | 11/1998 | Sequeira et al. | |
| 6,127,353 A | 10/2000 | Yuen et al. | |
| 6,841,146 B2 | 1/2005 | Haslwanter et al. | |
| D612,735 S * | 3/2010 | Leclair | D9/520 |
| 7,854,352 B2 | 12/2010 | Davies et al. | |
| D642,060 S * | 7/2011 | Leclair | D9/520 |
| 7,977,376 B2 | 7/2011 | Singh et al. | |
| 8,399,508 B2 | 3/2013 | Singh et al. | |
| 9,078,923 B2 * | 7/2015 | Dhuppad | A61K 47/36 |
| 2004/0097474 A1 | 5/2004 | Cagle et al. | |
| 2005/0158247 A1 * | 7/2005 | Veronesi | A61K 9/0043 514/7.7 |
| 2006/0110328 A1 | 5/2006 | Cagle et al. | |
| 2007/0099883 A1 | 3/2007 | Calis et al. | |
| 2007/0233012 A1 * | 10/2007 | Lerrick | A61M 15/0003 604/191 |
| 2008/0058296 A1 | 3/2008 | Chaudry | |
| 2008/0220107 A1 | 9/2008 | Akerman | |
| 2010/0276457 A1 * | 11/2010 | Petit | A61M 11/00 222/321.6 |
| 2012/0121653 A1 | 5/2012 | Jenkins et al. | |
| 2015/0079178 A1 | 3/2015 | Dhuppad et al. | |
| 2015/0099725 A1 | 4/2015 | Khairatkar-Joshi et al. | |
| 2015/0250718 A1 | 9/2015 | Dhuppad et al. | |
| 2016/0287612 A1 | 10/2016 | Dhuppad et al. | |

FOREIGN PATENT DOCUMENTS

| | | | |
|---|---|---|---|
| CN | 103826680 A | 8/2012 | |
| CN | 103285469 A | 9/2013 | |
| CN | 105307620 A | 2/2016 | |
| EP | 2014305 A1 | 1/2009 | |
| KR | 1020060131977 A | 3/2006 | |
| WO | WO-1995020393 A1 | 8/1995 | |
| WO | WO2001026658 | 4/2001 | |
| WO | WO-2001026658 | 4/2001 | |
| WO | WO-0189984 A1 * | 11/2001 | ......... B05B 11/0037 |
| WO | WO-2004043470 A1 | 5/2004 | |
| WO | WO-2006057769 A2 | 6/2006 | |
| WO | WO2007026151 | 3/2007 | |
| WO | WO2009003199 | 12/2008 | |
| WO | WO-2009003199 A1 | 12/2008 | |
| WO | WO-2010009028 A1 | 1/2010 | |
| WO | WO-2010025236 A1 | 3/2010 | |
| WO | WO-2011008923 A2 | 1/2011 | |
| WO | WO-2011141929 A2 | 11/2011 | |
| WO | WO-2012094283 A2 | 7/2012 | |
| WO | WO-2014092346 | 6/2014 | |
| WO | WO-2015036902 A1 | 3/2015 | |

OTHER PUBLICATIONS

Amrol, et al., Intranasal Steroids for Ocular Symptoms in Allergic Rhinitis, Hyperlink "http://www.jwatch.org/jw201006100000003/2010/06/10/intranasal-steroids-ocular-symptoms-allergic" http://www.jwatch.org/jw201006100000003/2010/06/10/intranasal-steroids-ocular-symptoms-allergic.
Aneeza et al., Allergy Rhinol, 2013, 4:e120-e126.
Anolik R., Allergy Asthma Proc, 2009, 30:406-412.
Anolik R., Int Arch Allergy Immunol, 2008, 147:323-330.
Anolik, et al., Clinical Benefits of Combination Treatment with Mometasone Furoate Nasal Spray and Loratadine vs Monotherapy with Mometasone Furoate in the Treatment of Seasonal Allergic Rhinitis, Ann Allergy Asthma Immunol., 2008, 100:264-271.
Austin, et al., Mometasone Furoate is a less specific Glucocorticoid than Fluticasone Propionate, European Respiratory Journal, 2002, 20:1386-1392.
Bajaj et al, The Internet Journal of Otohinolaryngology, 2006, vol. 6, No. 1.
Barnes, et al., Effects of Levocetirizine as Add-on Therapy to Fluticasone in Seasonal Allergic Rhinitis, Clinical and Experimental Allergy, 2006, 36:676-684.
Benincasa, et al., Evaluation of Fluticasone Propionate Aqueous Nasal Spray Taken Alone and in Combination with Cetirizine in the Prophylactic Treatment of Seasonal Allergic Rhinitis, Drug Invest. 1994, 8:4:225-233.
Bernstein et al., Respiratory Medicine, 1999, 93:603-612.
Bousquet, et al., Onset of Action of the Fixed Combination Intranasal Azelastine-Fluticasone Propionate in an Allergen Exposure Chamber, J Allergy Clin Immunol Pract, 2018, 1-7.e6 (13 pgs).
Buck, "Intranasal steroids for children with allergic rhinitis", Pediatric Pharmacology, May 2001, vol. 7, No. 5.
ClinicalTrials (Clinicaltrials.gov, firs! posted Aug. 17, 2016, last update posted May 4, 2017).

(56) References Cited

OTHER PUBLICATIONS

Derendorf et al, Eur Respir J, 2001, 17:157-158.
Di Lorenzo, et al., Randomized Placebo-controlled Trial Comparing Fluticasone Aqueous Nasal Spray in Mono-therapy, Fluticasone Aqueous Nasal Spray in Mono-therapy, Fluticasone Plus Cetirizine, Fluticasone Plus Montelukast and Cetirizine Plus Montelukast for Seasonal Allergic Rhinitis, Clin Exp Allergy, 2004, 34:259-267.
Dibildox, J Allergy Clin Immunol, 108(1):S54-S58.
Herbert et al., Allergy, 1996, 51:569-576.
International Search Report for International Application No. PCT/IB2015/065035 dated Jan. 9, 2015.
International Search Report for International Application PCT/IB2014/064251, dated Nov. 14, 2014, pp. 1-13.
International Search Report issued in PCT/US2018/040098 dated Sep. 25, 2018.
Johnson, M. Ph.D., Development of Fluticasone Propionate and Comparison with other Inhaled Corticosteroids, J. Allergy Clin. Immunol, 1998, 101:4:2:S434-S439.
Juniper, et al., Comparison of Beclomethasone Dipropionate Aqueous Nasal Spray, Astemizole, and the Combination in the Prophylatic Treatment of Ragweed Pollen-induced Rhinoconjunctivits, J Allergy Clin Immunol, 1989, 83:627-33.
LaForce et al., Allergy Asthma Proc, 2010, 31:132-140.
Maiti et al. (J of Pharmacology and Pharmacotherapeutics, Oct.-Dec. 2011, 2(4), 270-276).
Meltzer et al, Ann Allergy Asthma Immunol, 2005, 95:600-606.
Meltzer et al. (J Allergy Clin Immunol, Jul. 1998).
Meltzer et al., J Allergy Clin Immunol, 1999, 104(1):107-114.
Navarro et al., J Investig Allergol Clin Immunol, 2011, 21(5):363-369.
Nsouli, et al., Combination of a nasal antihistamine olopatadine and a nasal corticosteroid, mometasone . . . , International Scientific Conference, Dubai, UAE, Dec. 2010.
Okubo et al. (Current Medical Research and Opinion, 2010, 1657-1665).
Patel (Annals of Allergy, Asthma & Immunology, vol. 117, Issue 5, Supplement, Nov. 2016, pp. 114-115).
PR Newswire (http://www.prnewswire.com/news-releases/glenmark-pharmaceuticals-reports-positive-results-from-a-phase-3-trial-of-gsp-301-mometasoneolopatadine-fixed-dose-combination-nasal-spray-in-seasonal-allergic-rhinitis-300431125.html), Mar. 29, 2017.
Prenner, et al., Mometasone Furoate Nasal Spray Reduces the Ocular Symptoms of Seasonal Allergic Rhinitis, J Allergy Clin Immunol, Jun. 2010, 1247-1253.
Prescribing information for Nasonex® (Jan. 2011).
Prescribing information for Patanase® (Feb. 2012).
Ratner et al, J Fam Pract. 1998, 47(2):118-25.
Ratner, et al., Ann. Allergy Asthma Immunol, 2005, 95:474-479.
Roland, Expert Opin Pharmacother, 2010, 11(9), 1559-1567.
Simpson, Ann Allergy, 1994, 73:497-502.
U.S. Appl. No. 14/483,837, filed Sep. 11, 2014.
Anonymous: NCT02631551 on May 18, 2017: Clinical Trials.gov Archive, May 18, 2017 (May 18, 2017), XP055444418, Retrieved from the Internet: URL:https://clinicaltrials.gov/archive/NCT02631551/2017 0518 [retrieved on—Jan. 25, 2018].
Anonymous: NCT02870205 on May 3, 2017: ClinicalTrials.gov Archive, May 3, 2017 (May 3, 2017), XP055444415, Retrieved from the Internet: URL:https://clinicaltrials.gov/archive/NCT02870205/2017 0503 [retrieved on—Jan. 25, 2018] the whole document.
Anonymous: To Study GSP 301 in Patients With Seasonal Allergic Rhinitis—Study Results—ClinicalTrials.gov, Jun. 28, 2017 (Jun. 28, 2017), XP055445229, Retrieved from the Internet: URL:https://www.clinicaltrials.gov/ct2/show/results/NCT02318303?term=NCT02318303&rank=I=X4370156#othr [retrieved on Jan. 26, 2018] the whole document.
E.P. Terekhova, Allergic Rhinitis: Modern Methods of Treatment, 0.21518/2079-701X-2016-17-74-79, 2016, p. 74-79, 7 pages (with partial English translation).
Kagawa, et al., Synergetic Effects of Prednisiline and olo[atadine on atopic dermatituts model of hairless mice, Pharmacology, 2010, 85:5:286-294 (English Abstract).
Kaliner et al: Azelastine and olopatadine in the treatment of allergic rhinitis, Annals of Allergy, Asthma & Immunology, Arlington Heights, IL, US, vol. 103, No. 5, Nov. 1, 2009 (Nov. 1, 2009), pp. 373-380, XP026960456, ISSN: 1081-1206 [retrieved on Nov. 1, 2009] the whole document.
Search Report issued in European Patent Application No. 14802944.0 dated Mar. 1, 2023.
Anonymous , "Product Monograph Including Patient Medication Information Pr Ryal Tris (olopatadine hydrochloride and mometasone furoate nasal spray)", XP093025504, Retrieved from the Internet: URL: https://pdf.hres.ca/dpd_pm/00067564.PDF, Sep. 21, 2022.
Patel, Piyush , et al., "Effect of olopatadine-mometasone combination nasal spray on seasonal allergic rhinitis symptoms in an environmental exposure chamber study", Ann Allergy, Asthma, Immunol, Oct. 12, 2018, vol. 122, No. 2, XP085589177, 8 pages.

* cited by examiner

DISPENSING DEVICE AND PHARMACEUTICAL COMPOSITION FOR THE TREATMENT OF RHINITIS

This application is the U.S. national stage of International Patent Application No. PCT/US18/40098, filed Jun. 28, 2018, which claims the benefit of Indian Patent Application No. 201821014426, filed Apr. 16, 2018.

FIELD OF THE INVENTION

The present invention is directed to a dispensing device and pharmaceutical composition for nasal administration to a human for treatment of rhinitis; and more particularly to a dispensing device with pharmaceutical composition comprising mometasone, an ester thereof (e.g., mometasone furoate), or a salt thereof and olopatadine or a salt thereof (e.g., olopatadine hydrochloride).

BACKGROUND OF THE INVENTION

Rhinitis is a medical term for irritation and inflammation of the mucous membrane inside the nose. Rhinitis may cause additional symptoms, such as sneezing, nasal itching, coughing, headache, fatigue, malaise, and cognitive impairment. There is a need for an easy to use, efficient, reliable dispensing device with a pharmaceutical composition having superior efficacy in the treatment of rhinitis.

SUMMARY OF THE INVENTION

The present invention is directed to a dispensing device for nasal administration of a pharmaceutical composition containing mometasone, an ester thereof (e.g., mometasone furoate), or a salt thereof and olopatadine or a salt thereof (e.g., olopatadine hydrochloride). The dispensing device and pharmaceutical composition are particularly suitable for the treatment of allergic rhinitis in a human subject. The combination of dispensing device and pharmaceutical composition achieves consistent dosing of the mometasone and olopatadine components. In one embodiment, the compositions comprises mometasone furoate and olopatadine hydrochloride.

In one embodiment, a dispensing device and pharmaceutical composition for nasal administration to a human subject includes (a) a container for the pharmaceutical composition; (b) a dispenser head for dispensing the pharmaceutical composition from the container, the dispenser head including at least a pump or valve mechanism, a dispensing channel, and a dispensing orifice; (c) a dip tube extending along the longitudinal axis of the container, the dip tube having a proximal end communicating with the dispenser head and an open distal end extending into the container; and (d) a pharmaceutical composition in the container and in communication with the distal end of the dip tube, where the pharmaceutical composition comprises mometasone, an ester thereof, or a salt thereof and olopatadine or a salt thereof. In one embodiment, the pharmaceutical composition is an aqueous suspension containing a hydrocolloid, where the mometasone is present in particulate form and the olopatadine is in dissolved form. In a preferred embodiment, the pharmaceutical composition comprises a suitable amount of hydrocolloid such that the pharmaceutical composition has a viscosity of 10 cps to about 200 cps or preferably from about 20 cps to about 150 cps. The pharmaceutical composition may comprise about 0.001% w/w to about 0.075% w/w mometasone, an ester thereof (e.g., mometasone furoate), or a salt thereof in particulate form, and about 0.5% w/w to about 0.8% w/w olopatadine or a salt thereof (e.g., olopatadine hydrochloride) in dissolved form. A cap to cover a tip of the dispensing head may also be included.

In one aspect, the container has a conically shaped internal bottom, where the internal bottom is angled downwardly from a side of the container toward a center. The center is located along a longitudinal axis of the container. The internal bottom can include a further angularly deepened well centrally located about the longitudinal axis, where the center is a low point of the internal bottom of the container. In this aspect, the distal end of the dip tube can extend into the well, or can be located at a top of the well.

In another aspect, the well of the internal bottom of the container can further include a groove therein. The groove further deepens an internal bottom of the well and extends across the longitudinal axis of the container. Accordingly, the internal bottom of the well, at the center, is the low point of the internal bottom of the container. In this aspect, the open distal end of the dip tube can extend into the groove or can be located at a top of the groove. Also in this aspect, a dimension of the groove, that further deepens the internal bottom of the well, does not affect an external bottom of the well, as a deepening dimension of the groove is within a wall thickness of the bottom of the well.

In still another aspect, at least the well of the internal bottom of the container further includes a groove therein. This groove further deepens an internal bottom of the well in a dimension greater than a wall thickness of the bottom of the well, thereby requiring modification of an external bottom of at least the well. In this aspect, a support bead, with the groove therein, extends from at least an external bottom of the well. The support bead also extends across the longitudinal axis of the container. In this aspect, the open distal end of the dip tube can extend into the groove or can be located at a top of the groove.

In a further aspect, the dispenser head is defined exteriorly by at least an end or tip wall and a lateral wall. The end wall has the dispensing orifice included therein. In this aspect, the cap is releasably attachable to the dispenser head for covering at least the dispensing orifice. The cap includes a sealing sleeve that can extend from an interior surface of the cap and communicate in a leak tight or seal tight manner with a perimeter of the lateral wall of the dispenser head.

In a still further aspect, an inner diameter of a distal end of the sealing sleeve is smaller than an exterior diameter of the lateral wall of the dispenser head, at a point of communication of the sealing sleeve with the lateral wall. This relationship assists to create the seal tight manner in which the cap and dispenser head engage in the closed position. In this engagement, the distal end of the sealing sleeve is radially deformed.

In this or another aspect, the sealing sleeve can have a wall thickness that decreases as the sealing sleeve extends away from the inside of the cap. The cap could further include, on an interior thereof, one or more protruding tabs that snap fit against the lateral wall of the dispenser head to hold the cap securely on the dispenser head in the closed position.

The above and below recited features of the various components of the dispensing device can be selectively combined in various permutations, each being contemplated herein. Also, the below recited features of the pharmaceutical composition can be selectively chosen for use with the dispensing device.

In one aspect, the pharmaceutical composition includes about 0.001% w/w to about 0.075% w/w mometasone, an ester thereof (e.g., mometasone furoate), or a salt thereof in particulate form and about 0.5% w/w to about 0.8% w/w olopatadine or its salt (e.g., olopatadine hydrochloride) in dissolved form. In this aspect, the composition could further include a hydrocolloid system, for example, in an amount sufficient to inhibit phase separation for at least 24 hours when stored at 25±2° C. and 60%±5% relative humidity. In one embodiment, the composition when stored for up to 12 months at 25±2° C. and 60%±5% relative humidity in the dispensing device contains has one or more of the following properties:

(i) the composition contains not more than 1% of total impurities (after storage);

(ii) the composition contains not more than 1% of DMC (after storage);

(iii) the composition contains not more than 1% of DMCF (after storage);

(iv) the composition contains not more than 1% of α-hydroxy olopatadine (after storage);

(v) the composition contains not more than 1% of olopatadine E-isomer (after storage);

(vi) the composition contains not more than 1% of Olopatadine Related Compound B (after storage); and/or (vii) the composition contains not more than 0.42% of other impurities of olopatadine (after storage).

In another aspect, the pharmaceutical composition includes about 0.025% w/w to about 0.05% w/w mometasone, an ester thereof (e.g., mometasone furoate), or a salt thereof in particulate form; and about 0.5% w/w to about 0.8% w/w olopatadine or its salt (e.g., olopatadine hydrochloride). In still another aspect, the pharmaceutical composition includes about 0.025% w/w to about 0.05% w/w mometasone, an ester thereof (e.g., mometasone furoate), or a salt thereof in particulate form; and about 0.6% w/w to about 0.7% w/w olopatadine or its salt. The pharmaceutical composition may further include a hydrocolloid as described above.

In still another aspect, the dispensing device dispenses about 100 µl of the pharmaceutical composition per actuation, wherein a single actuation dispenses about 665 mcg of olopatadine hydrochloride and about 25 mcg or about 50 mcg of mometasone furoate (preferably 25 mcg mometasone furoate).

More generally, the dispensing device can include a container, a cap, and a dispenser head which can include a pump, a dip tube, a valve, an actuator, a dispensing channel and a dispensing orifice. The pump is designed to dispense the pharmaceutical composition through the dip tube into the valve, through the actuator fitted with the dispensing orifice. The pharmaceutical composition is released in the form of a uniform spray. Valves can be continuous spray valves and/or metering valves. Valves can operate in tandem with the actuator which allow for easy opening and closing of the valve and provide for a desired spray characteristic. Actuators include, but are not limited to, spray actuators, foam actuators, solid-stream actuators, and special actuators. The dispensing device delivers a nasal spray in a uniform dose of, for instance, mometasone (e.g., as mometasone furoate) and olopatadine (e.g., as olopatadine hydrochloride), where the dose is dispensed every time the dispensing device is actuated by a user.

The dispensing device may require priming for about 2-6 actuations to consistently dispense the composition. The droplet size of the nasal spray can be controlled by the size of the dispensing orifice of the container. The dispensing orifice size also influences characteristics of the spray pattern.

In one aspect, the pharmaceutical composition, when delivered as a nasal spray by the dispensing device, has a spray pattern having a longest axis of about 15-75 mm, a shortest axis of about 10-65 mm, and an ellipticity of about 1-2.

BRIEF DESCRIPTION OF THE DRAWINGS

The present invention will be better understood with reference to the following description taken in combination with the drawings. For the purpose of illustration, there are shown in the drawings certain embodiments of the present invention. In the drawings, like numerals indicate like elements throughout. It should be understood, however, that the invention is not limited to the precise arrangements, dimensions, and instruments shown.

DETAILED DESCRIPTION OF THE INVENTION

Figure 1:
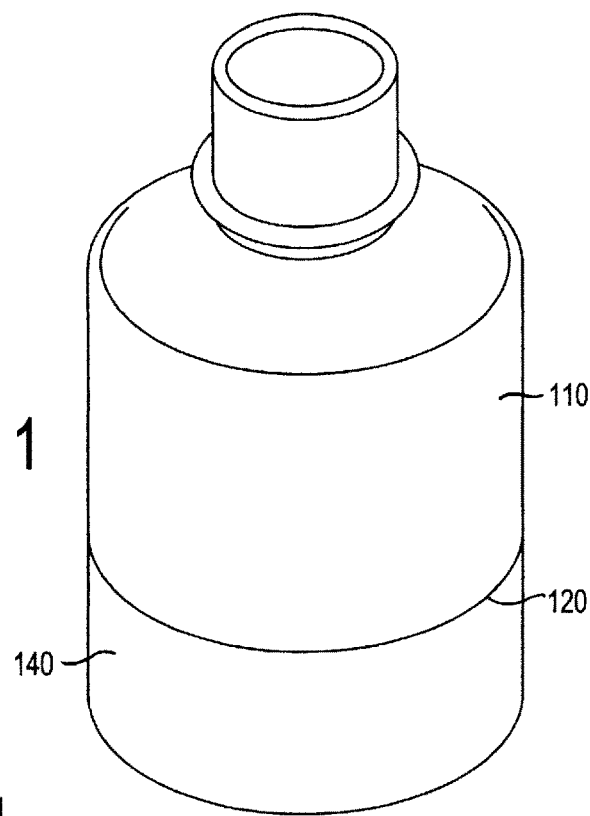
FIG. 1 illustrates one embodiment of a container of the dispensing device and pharmaceutical composition of the present invention, the container having a flat bottom.

The present invention is directed to a dispensing device and pharmaceutical composition for nasal administration to a human for treatment of rhinitis; and more particularly to a dispensing device with pharmaceutical composition comprising mometasone, an ester thereof, or a salt thereof and olopatadine or its salt.

In one embodiment, a dispensing device and pharmaceutical composition for nasal administration to a human includes (a) a container for the pharmaceutical composition; (b) a dispenser head for dispensing the pharmaceutical composition from the container, the dispenser head including at least a pump or valve mechanism, a dispensing channel, and a dispensing orifice; (c) a dip tube extending along the longitudinal axis of the container, the dip tube having a proximal end communicating with the dispenser head and an open distal end extending into the container; and (d) a pharmaceutical composition in the container and in communication with the distal end of the dip tube, where the pharmaceutical composition comprises mometasone, an ester thereof (e.g., mometasone furoate), or a salt thereof and olopadatinc or a salt thereof (e.g., olopatadine hydrochloride). In one embodiment, the pharmaceutical composition is an aqueous suspension containing a hydrocolloid, where the mometasone, an ester thereof (e.g., mometasone furoate), or a salt thereof is present in particulate form and the olopatadine or a salt thereof (e.g., olopatadine hydrochloride) is in dissolved form. In a preferred embodiment, the pharmaceutical composition comprises a suitable amount of hydrocolloid such that the pharmaceutical composition has a viscosity of 10 cps to about 200 cps or preferably from about 20 cps to about 150 cps. The pharmaceutical composition may comprise about 0.001% w/w to about 0.075% w/w mometasone, an ester thereof (e.g., mometasone furoate), or a salt thereof in particulate form, and about 0.5% w/w to about 0.8% w/w olopatadine or its salt (e.g., olopatadine hydrochloride) in dissolved form. A cap to cover a tip of the dispensing head may also be included.

In one aspect, the container can have a conically shaped internal bottom, where the internal bottom is angled downwardly from a side of the container toward a center. The center is located along a longitudinal axis of the container. The internal bottom can include a further angularly deepened well centrally located about the longitudinal axis, where the center is a low point of the internal bottom of the container. In this aspect, the distal end of the dip tube can extend into the well, or can be located at a top of the well.

In another aspect, the dispenser head is defined exteriorly by at least an end or tip wall and a lateral wall. The end wall has the dispensing orifice included therein. In this aspect, the cap is releasably attachable to the dispenser head for covering at least the dispensing orifice. The cap includes a sealing sleeve, extending from an interior surface of the cap, that communicates in a leak tight or seal tight manner with a perimeter of the lateral wall of the dispenser head.

In a further aspect, the pharmaceutical composition includes about 0.001% w/w to about 0.075% w/w mometasone, an ester thereof (e.g., mometasone furoate), or a salt thereof in particulate form and about 0.5% w/w to about 0.8% w/w olopatadine or its salt (e.g., olopatadine hydrochloride) in dissolved form. In this aspect, the composition could further include a hydrocolloid system, for example, in an amount sufficient to inhibit phase separation for at least 24 hours when stored at 25±2° C. and 60% 5% relative humidity. In one embodiment, the composition when stored for up to 12 months at 25±2° C. and 60%±5% relative humidity in the dispensing device contains has one or more of the following properties:

(i) the composition contains not more than 1% of total impurities (after storage);
(ii) the composition contains not more than 1% of DMC (after storage);
(iii) the composition contains not more than 1% of DMCF (after storage);
(iv) the composition contains not more than 1% of α-hydroxy olopatadine (after storage);
(v) the composition contains not more than 1% of olopatadine E-isomer (after storage);
(vi) the composition contains not more than 1% of Olopatadine Related Compound B (after storage); and/or
(vii) the composition contains not more than 0.42% of other impurities of olopatadine (after storage).

In a still further aspect, the pharmaceutical composition includes about 0.025% w/w to about 0.05% w/w mometasone, an ester thereof (e.g., mometasone furoate), or a salt thereof in particulate form; and about 0.5% w/w to about 0.8% w/w olopatadine or its salt (e.g., olopatadine hydrochloride). In this aspect, the pharmaceutical composition could further include a hydrocolloid.

Generally, the dispensing device can include a container, a cap, and a dispenser head which can include a pump, a dip tube, a valve, an actuator, a dispensing channel and a dispensing orifice. The pump is designed to dispense the pharmaceutical composition through the dip tube into the valve, through the actuator fitted with the dispensing orifice. The pharmaceutical composition is released in the form of a uniform spray. Valves can be continuous spray valves and/or metering valves. Valves can operate in tandem with the actuator which allow for easy opening and closing of the valve and provide for a desired spray characteristic. Actuators include but are not limited to spray actuators, foam actuators, solid-stream actuators, and special actuators. The dispensing device delivers a nasal spray in a uniform dose of mometasone (e.g., mometasone furoate) and olopatadine (e.g., olopatadine hydrochloride), where the dose is dispensed every time the dispensing device is actuated by a user.

In one aspect, the dispensing device dispenses about 100 µl of the pharmaceutical composition per actuation, where a single actuation dispenses about 665 mcg of olopatadine hydrochloride and about 25 mcg or about 50 mcg of mometasone furoate, preferably about 25 mcg mometasone furoate.

In another aspect, the dispensing device may require priming for about 2-6 actuations to consistently dispense the composition. The droplet size of the nasal spray can be controlled by the size of the dispensing orifice of the container. The dispensing orifice size also influences characteristics of the spray pattern.

Definitions

The term "effective amount" when used in connection with an active ingredient denotes an amount of the active ingredient that, when administered to a subject for treating rhinitis, produces an intended therapeutic benefit in a subject. The term "active ingredient" (used interchangeably with "active" or "active substance" or "drug") as used herein includes mometasone furoate or its salt and olopatadine or its salt. The effective amount of mometasone furoate or its salt can range from about 0.01 mg to about 10 mg or preferably from about 0.02 mg to about 5 mg. The effective amount of olopatadine or its salt can range from about 0.05 mg to about 20 mg, or preferably from about 0.1 mg to about 15 mg.

In an aspect of this invention, for daily administration by the nasal route, the effective amount of mometasone furoate or its salt can range from about 10 mcg to about 500 mcg, or preferably from about 20 mcg to about 400 mcg, and that for olopatadine or its salt can ranges from about 50 mcg to about 7000 mcg, or preferably from about 100 mcg to about 5400 mcg.

By "salt" or "pharmaceutically acceptable salt", it is meant those salts which are, within the scope of sound medical judgment, suitable for use in contact with the tissues of humans and lower animals without undue toxicity, irritation, and allergic response, commensurate with a reasonable benefit to risk ratio, and effective for their intended use. Representative acid additions salts include hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, ascorbate, glucoheptonate, lactobionate, and lauryl sulphate salts. Representative alkali or alkaline earth metal salts include sodium, calcium, potassium and magnesium salts.

The term "treating" or "treatment" as used herein includes the prophylaxis, mitigation, prevention, amelioration, or suppression of a disorder modulated by mometasone, an ester thereof, or a salt thereof or olopatadine or its salt, or by a combination of the two in a mammal.

By "pharmaceutically acceptable excipients", it is meant any of the components of a pharmaceutical composition other than the active ingredients and which are approved by regulatory authorities or are generally regarded as safe for human or animal use.

As used herein, the term "average particle size" (or synonymously, "mean particle size") refers to the distribution of particles, wherein about 50 volume percent of all the particles measured have a size less than the defined average particle size value and about 50 volume percent of all particles measured have a particle size greater than the defined average particle size value. This can be identified by the term "$D_{50}$" or "$d_{(0.5)}$". The average particle size can be measured using various techniques such as microscopy, laser diffraction, photon correlation spectroscopy (PCS) and Coulter's principle.

The "hydrocolloid" refers to a colloid system wherein hydrophilic colloid particles (e.g., hydrophilic polymers) are dispersed in water. The hydrocolloid system can exist in gel state or sol (liquid) state. In suspension compositions, the hydrocolloids function as thickening, stabilizing and suspending agents. Non-limiting examples of hydrocolloid include xanthan gum, gum arabic, guar gum, locust bean gum, alginate, starch, agar-agar, carrageenan, gelatin, Avicel RC591® (mixture of microcrystalline cellulose & sodium carboxymethyl cellulose) and cellulose derivatives (e.g., carboxymethyl cellulose sodium). Preferably, the hydrocolloid includes xanthan gum or carboxymethylcellulose sodium.

As used herein, the term "α-hydroxy olopatadine" of olopatadine refers to "(Z)-2-{11-[3-(Dimethylamino) propylidene]-6,11-dihydrodibenz[b,e]oxepin-2-yl}-2-hydroxy-acetic acid".

As used herein, the term "Olopatadine E-Isomer" refers to "11-[(E)-3-(Dimethylamino)propylidene]-6,11-dihydrodibenz[b,e]oxepin-2-acetic acid".

As used herein, the term "Olopatadine Related Compound B" refers to "(Z)-3-{2-(Carboxymethyl)dibenzo[b.e]oxepin-11(6H)-ylidene}-N,N-dimethylpropan-1-amine oxide".

As used herein, the term "8-DM" of mometasone refers to "(9β,11β-epoxy-17α,21-dihydroxy-16α-methyl pregna-1,4-dience-3,20-dione)".

As used herein, the term "DMC" of mometasone refers to "(21-chloro-9β,11β-epoxy, 17α,-hydroxyl-16α-methyl pregna-1,4-dience-3,20-dione)".

As used herein, the term "DMCF" of mometasone refers to "(21-chloro-9β,11β-epoxy-16α-methyl-3,20-dioxo pregna-1,4-dien-17ylfuran-2-carboxylate)".

The "onset of action" is the point at which patients might reasonably expect to see a meaningful decrease in their allergic rhinitis symptoms (such as a meaningful decrease in reflective total nasal symptom score (rTNSS), instantaneous total nasal symptom score (iTNSS) or reflective total ocular symptom score (rTOSS)). Statistically, it is the first time point after initiation of treatment when the drug demonstrates a change greater than the placebo treatment from baseline in the primary efficacy endpoint. This statistically significant difference between drug and placebo is maintained for some period (e.g., for 4 hours) from this point onward. See "Guidance for Industry, Allergic Rhinitis: Clinical Development Programs for Drug Products". U.S. Department of Health and Human Services. Food and Drug Administration, Center for Drug Evaluation and Research (CDER), April 2000.

The term "faster onset of action" refers, in one embodiment, to a statistically significant faster reduction in one or more parameters associated with the treatment of allergic rhinitis in a subject, such as a statistically significant faster reduction in reflective total nasal symptom score (rTNSS), instantaneous total nasal symptom score (iTNSS) or reflective total ocular symptom score (rTOSS) of the subject.

The term "advertising" refers to notifying, informing, and/or apprising one or more individuals of information (e.g., the efficacy or time for onset of action of a pharmaceutical product for treating or reducing an indication), such as by mass media, including, but not limited to, newspaper, magazine, and internet advertisements, television commercials, and billboard signs. The term "advertising" as used herein also includes including a statement that the pharmaceutical product can treat or reduce the indication in the labeling for the pharmaceutical product.

The term "marketing" refers to the act or process of selling a product, including, but not limited to, any offer for sale or sale of a product, as well as advertising.

Dispensing Device

The dispensing device for nasal administration to a human includes (a) a container for the pharmaceutical composition; (b) a dispenser head for dispensing the pharmaceutical composition from the container, the dispenser head including at least a pump or valve mechanism, a dispensing channel, and a dispensing orifice; and (c) a dip tube extending along the longitudinal axis of the container, the dip tube having a proximal end communicating with the dispenser head and an open distal end extending into the container. A cap may or may not be included.

The container of the dispensing device can be a round or oval; preferably, the container is round. The container can further have a flat bottom or a generally conically shaped bottom. The conically shaped bottom is angled downwardly from a side of the container to a center of the bottom, the center being a low point of the bottom of the container. The center of the bottom is preferably located along a longitudinal axis of the container.

A dip tube is located within the container. In the flat bottom embodiment of the container, the distal (open) end of the dip tube is located near the flat bottom. In the conically shaped embodiment of the container, the distal end of the dip tube is located in the conically shaped portion (down in the low point) of the container. Locating the distal end of the dip tube as close as possible to the low point of the bottom of the container assists in avoidance of dead volume residue in the container during multiple actuations (especially when the container nears exhaustion).

The generally conically shaped bottom can further have a support bead or an angularly deepened well located about the longitudinal axis, between the side and the center of the container, resulting in the center providing an even lower point to an internal bottom of the container. Accordingly, the well accommodates the distal end of the dip tube to more effectively reduce any dead volume residue.

The flat bottom, the conically shaped bottom, and the conically shaped bottom with deepened well, can each accommodate and rest onto a base cup having a flat, closed bottom. The base cup can snap-fit against a bottom of the container, where an upper, open end of the base cup is equipped to accommodate the respective bottom of the container.

FIG. 1 illustrates one container embodiment of the dispensing device of the present invention. The container 110 has a flat bottom 120. The flat bottom 120 of the container 110 rests onto a base cup 140 which has a flat exterior bottom surface to secure the container for easy storage.

Figure 2:
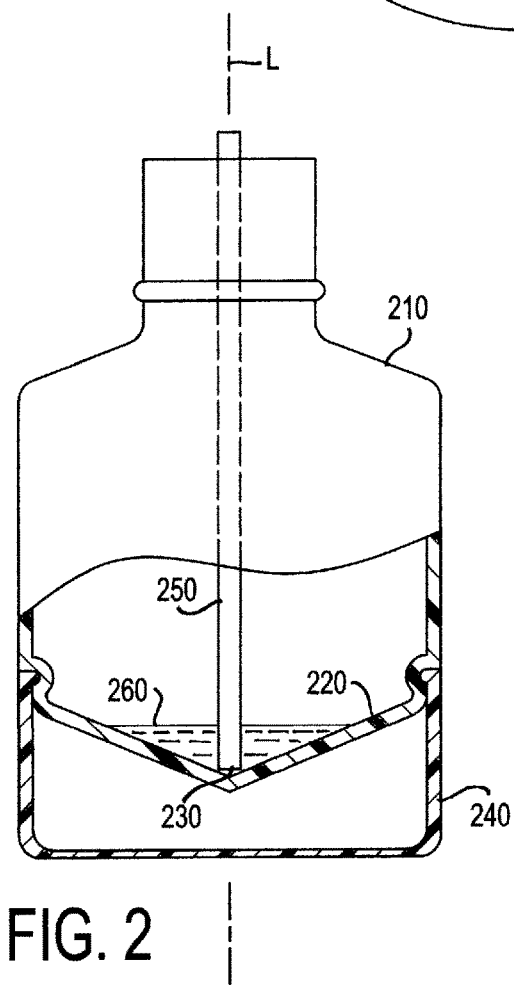
FIG. 2 illustrates a cross-section of another embodiment of a container of the dispensing device and pharmaceutical composition of the present invention, the container having a conically shaped bottom.

FIG. 2 illustrates another container embodiment of the dispensing device. The container 210 has a conically shaped bottom 220 having an internal low point 230. The low point 230 can accommodate residual volume of the pharmaceutical composition 260. The conically shaped bottom 220 is shown resting on a base cup 240 having a flat bottom surface to secure the container in place.

A dip tube 250 is located within the container 210 and has a distal (open) end located in the low point 230 of the container 210. This specific configuration of the conically shaped bottom 220, having the distal end of the dip tube 250 as close as possible to the low point 230 of the conically shaped bottom 220, allows for low residual volumes of pharmaceutical composition 260, upon multiple actuations of the dispensing device, to provide a dose volume, especially when content of the container 210 nears exhaustion.

Figure 3:
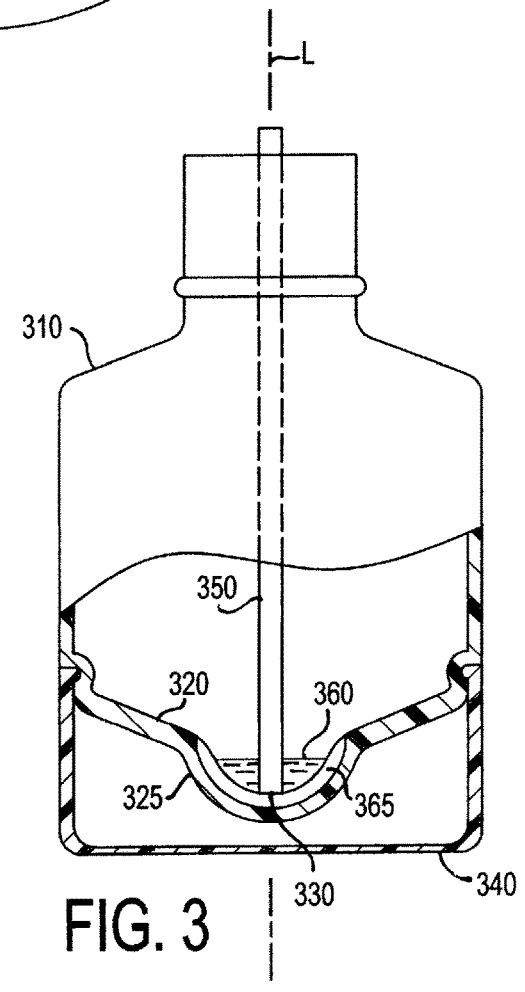
FIG. 3 illustrates a cross-section of still another embodiment of a container of the dispensing device and pharmaceutical composition of the present invention, the container having a conically shaped bottom with an angularly deepened well.

FIG. 3 illustrates a further container embodiment of the dispensing device. The container 310 has a generally conically shaped bottom 320 having an angularly deepened well 325 located about a longitudinal axis L of the container 310. The well 325, deepening between a side of the container 310 and the center of the container 310, results in the center providing a low point 330 to an internal bottom of the container 310. Again, the low point 330 can accommodate residual volume of the pharmaceutical composition 360. This embodiment is again shown resting on a base cup 340 having a flat bottom surface to secure the container in place.

In a still further container embodiment of the dispensing device, as shown in FIG. 3, a bottom of the well 325 has a groove 365 internally located therein. The groove 365 further deepens an internal bottom of the well 325. In this embodiment, a dimension of the groove 365 does not affect an external bottom of the well 325 (or container 310). As shown in FIG. 3, an external bottom of the container 310 takes a shape and contour of the well 325. The height (or deepening dimension) of the groove 365 is within a wall thickness of a bottom of the well 325 (and container 310). Within the well 325, the groove 365 extends laterally across the longitudinal axis L of the container 310.

A dip tube 350 is located within the container 310. In the container 310 embodiment having the well 325 only (that is, without a groove 365 within the well 325), the distal (open) end of the dip tube 350 is located in the low point 330 of the well 325. In the container 310 embodiment having the well 325 with internal groove 365 therein, the distal (open) end of the dip tube 350 extends into the groove 365, or extends to the internal bottom of the well 325 (just at a top of the groove 365, as shown in FIG. 3). A bottom of the groove 365, located at the longitudinal axis L of the container 310, becomes a low point 330 for the composition 360 in the container 310. The dip tube 350, extending into the groove 365, or extending to the internal bottom of the well 325 (just at a top of the groove 365), allows that low residual volumes of pharmaceutical composition 360, upon multiple actuations of the dispensing device, provides an adequate dose volume, especially when a content of the container 310 nears exhaustion.

Figure 4A:
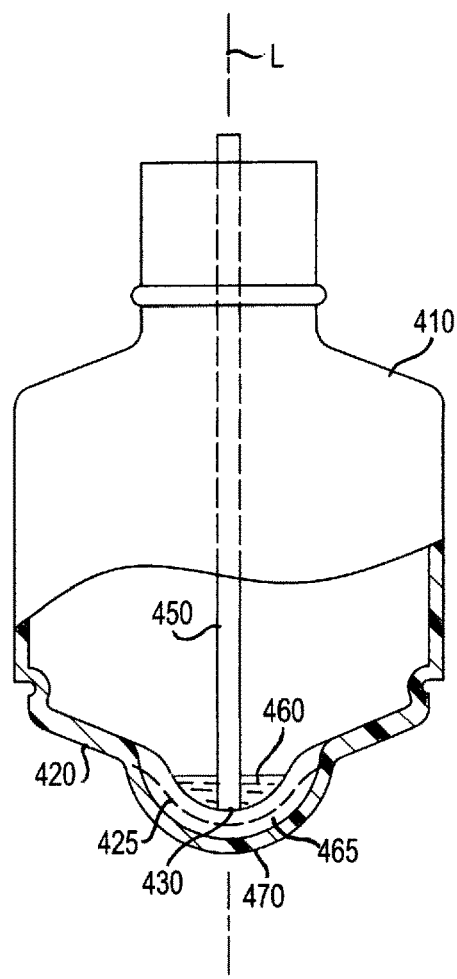
FIGS. 4A and 4B illustrate a cross-section and a bottom perspective view, respectively, of a further embodiment of a container of the dispensing device and pharmaceutical composition of the present invention, the container having a conically shaped bottom with an angularly deepened well comprising a groove extending below a bottom of the well, in FIG. 4A, and a support bead shown externally below the well in FIG. 4I.
Figure 4B:
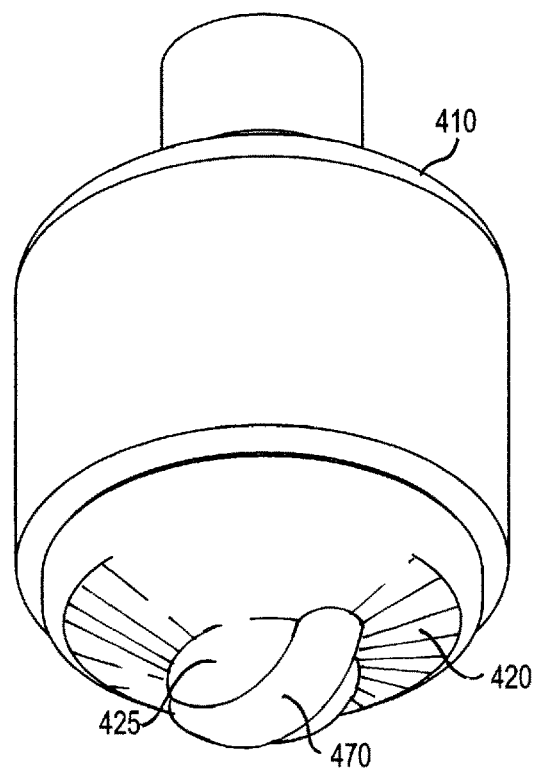

FIG. 4A illustrates a cross-section of a still further container embodiment of the dispensing device. FIG. 4B illustrates an external, bottom perspective view of a container embodiment of the dispensing device, the external container embodiment shown in FIG. 4B can be used with one or more of the internal container embodiments described above and below (e.g., the external container embodiment of FIG. 4B can be used with the internal container embodiments of FIG. 3 or FIG. 4A).

In the cross-section FIG. 4A, the container 410 has a conically shaped bottom 420 having an angularly deepened well 425 located about a longitudinal axis L of the container 410. The well 425, deepening between a side of the container 410 and the center of the container 410, results in the center providing a low point 430 to an internal bottom of the container 410. In this embodiment, a groove 465 extends below a bottom of the well 425 (shown in dotted lines in FIG. 4A), deepening the low point 430 of the internal bottom of the container 410 below the bottom of the well 425.

In this aspect, where the groove 465 extends below the bottom of the well 425, requires an extension of an external bottom of the container 410. Accordingly, a support bead 470 is externally located about a bottom of the well 425, as shown in FIG. 4B, further deepening the external bottom of the well 425. In this embodiment, the groove 465 laterally extends, across the longitudinal axis L of the container 410, in a dimension greater than a diameter of the deepened well 425. As shown best in FIG. 4B, an external bottom of the container 410 takes a shape and contour of the support bead 470 rounded about the (semi-circular) well 425.

As shown in FIG. 4A, a dip tube 450 is located within the container 410, and has a distal (open) end extending into the groove 465, or extending to the bottom of the well 425 (just at a top of the groove 465, as shown in FIG. 4A). An internal bottom of the groove 465, located at the longitudinal axis L of the container 410, becomes a low point 430 for the composition 460 in the container 410. The dip tube 450, extending into the groove 465, or extending to the bottom of the well 425 (just at a top of the groove 465), allows that low residual volumes of pharmaceutical composition 460, upon multiple actuations of the dispensing device, provides a dose volume, especially when a content of the container 410 nears exhaustion.

As noted above, the external embodiment of the container 410, shown in FIG. 4B, can include the internal embodiment of the container 410 shown in FIG. 4A, or can include the internal embodiment of the container 310 shown in FIG. 3. The external embodiment of FIG. 4B, including support bead 470, provides structural support to a container bottom regardless of internal container embodiment employed. For example, in FIG. 3, the support bead 470 provides structural support to an external bottom of the container 310, where a wall thickness of a bottom of the well 325 is lessened because of the groove 365. In FIG. 4A, the support bead 470 is necessary because the groove 465 is deepened below a normal bottom of the well 425. In this aspect, the present invention contemplates an addition of a support bead to an external bottom of a container regardless of the characteristics of the internal bottom of the respective container.

The container can be made of any polymeric substance. In such embodiments, suitable polymers include, but are not limited to, polyethylene, polypropylene (PP), polystyrene (PS), nylon (Ny), polyvinyl chloride (PVC), polyethylene terephthalate (PET), polycarbonate (PC), polyoxymethylene (POM), polysulfone (PSF), polyethersulfone (PES), polyacrylate (PAR), and polyamide (PA). In certain embodiments, the polymer is polyethylene, particularly medium-density polyethylene (MDPE) (or branched polyethylene) or high density polyethylene (HDPE) (or linear, polyethylene). In one embodiment, the bottle is made of high density polyethylene (HDPE).

The container may have an inert coating on an inner surface thereof to avoid any interaction of the container component with the pharmaceutical compositions of the present invention.

The dispensing device of the present invention further comprises a cap equipped to cover a dispensing head of the dispensing device. The cap is made of polymeric substances, as described above. Preferably, the cap is an Antilop cap also known as Anti-Loss On Priming cap. The cap has a sealing element extending from an inside of a top wall thereof, the sealing element providing a sealing between the cap and an dispensing orifice of the dispensing head. The sealing element arrangement about a distal tip of the dispensing head, and about the dispensing orifice of the dispensing head, prevents the distal tip of the dispensing head from drying and prevents misfiring of the pharmaceutical composition from the dispensing head upon accidental actuation.

Figure 5A:
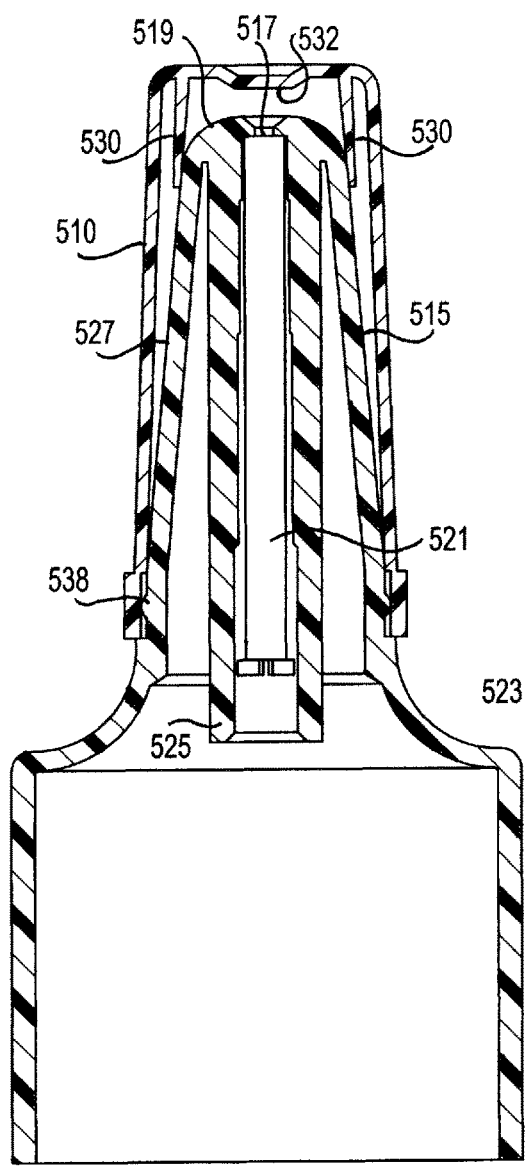
FIGS. 5A and 5B illustrate a cross-section and a partial exploded view, respectively, of one embodiment of a protective cap of the dispensing device and pharmaceutical composition of the present invention, the cap shown in a closed position on a dispenser head.
Figure 5B:
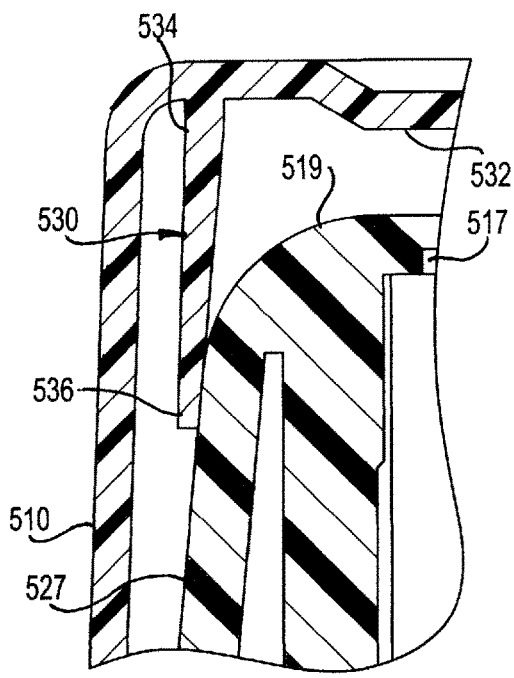

FIGS. 5A and 5B illustrate a cross-section and a partial exploded view, respectively, of a protective cap 510 of the present invention on a dispenser head 515. The exploded view in FIG. 5B is a partial portion of FIG. 5A. FIGS. 5A and 5B show the cap in a closed, seal or leak tight position on the dispenser head 515. The dispenser head 515 can be frustoconical in shape, but generally has a shape of a typical nasal-spray actuator.

A distal end of the dispenser head 515 includes a dispensing orifice 517 in a tip or end wall 519 of the dispenser head 515, the dispensing orifice 517 being located at an end of a dispensing channel 521. At a proximal end of the dispenser head 515 is an actuating surface 523 for actuating the dispensing device, along with a connector 525 for connecting the dispenser head 515 to a pump or a valve (not shown). Adjacent to the tip or end wall 519 of the dispenser head 515 is a lateral wall 527 of the dispenser head 515, there being rounded edge therebetween.

The cap 510 includes a sealing element or sleeve 530 that projects from an inside of a top wall 532 of the cap 510. The sealing element 530 can be a ring-shaped sealing flange or sleeve. The sealing element 530 communicates in a leak or seal tight manner with the lateral wall 527 of the dispenser head 515 when the cap 510 is in the closed position. The sealing element 530 can be integral with the cap.

The sealing element or sleeve 530 may have a thickness that decreases as the sealing element extends away from the inside of the top wall 532 of the cap 510, as readily shown in FIG. 5B where the sealing element 530 is thicker at a proximal end 534 (at a point of connection with the inside of the top wall 532 of the cap 510) than at a distal end 536. The sealing element 530 provides flexibility to ensure a seal or leak tight communication with the lateral wall 527 of the dispenser head 515. Upon closure of the cap 510, the distal end 536 of the sealing element 530 communicates with the lateral wall 527 by friction fit to create the seal or leak tight fit. In one embodiment, an inner diameter of the distal end 536 of the sealing element 530 is smaller than an exterior diameter of the lateral wall 527 of the dispenser head 515, at a point of communication of the sealing element 530 with the dispenser head 515, to ensure a seal tight fit between the sealing element 530 and the dispenser head 515. In this instance, and due to a flexibility of the distal end 536 of the sealing element 530, the distal end 536 of the sealing element 530 is radially deformed when the cap 510 is in the closed position.

An interior of the cap 510, and/or the exterior of the lateral wall 527 of the dispenser head 515, can further include one or more tabs 538 that snap fit against engaging detents to hold the cap 510 securely on the dispenser head 515 when the cap 510 is in the closed position. With the cap 510 in a secure, closed position on the dispenser head 515, the inside of the top wall 532 of the cap 510 does not contact tip wall 519 of the dispenser head 515. Only the sealing element 530 contacts, in a leak or seal tight manner, the lateral wall 527 of the dispenser head 515.

Accordingly, with the cap 510 in a closed position, only a small amount of air is contained between the tip wall 519 of the dispenser head 515, the inside of the top wall 532 of the cap 510, and the sealing element 530. This amount of air prevents any fluid from evaporating and/or drying inside the dispensing orifice 517.

Figure 6:
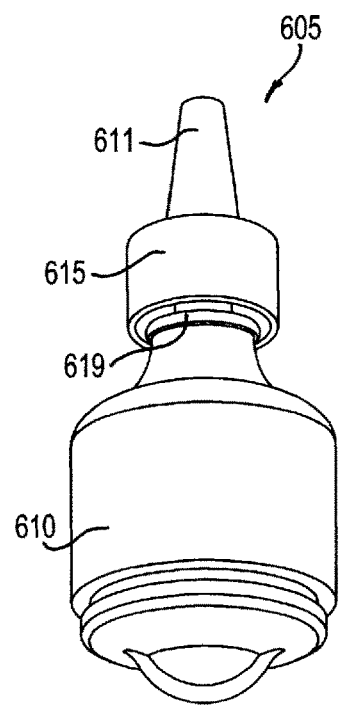
FIG. 6 illustrates one embodiment of a dispensing device of the dispensing device and pharmaceutical composition of the present invention.

FIG. 6 illustrates one embodiment of the dispensing device 605 of the present invention. The dispensing device 605 shown in FIG. 6 includes an optional cap 611, a container 610, a dispenser head 615, a pump 619, and a dip tube 650 (not seen in FIG. 6). The pump 619 is adequate to dispense a stable fixed dose pharmaceutical composition of the present invention from the container 610, through the dip tube 650 (not seen in FIG. 6), into the dispenser head 615, and out a dispensing orifice. A valve can be included to release the composition from the dispensing orifice in the dispenser head in the form of a spray. The pump 619 may comprise a pre-compression pump, such as the VP3 or VP7 model, or a modified version thereof, manufactured by Valois SA. For example, the dispensing device 605 is adequate to dispense a nasal spray of uniform dosage of mometasone (e.g., mometasone furoate) and olopatadine (e.g., olopataine hydrochloride) every time the dispensing device is actuated by a user.

The dispensing device 605 can comprise a valve to release a spray of the stable fixed dose composition from the dispensing orifice. Valves can include, but are not limited to, continuous spray valves and metering valves. Opening and closing of a valve is facilitated by actuation of the dispenser head. Various types of actuation include, but are not limited to, spray actuators, foam actuators, solid-stream actuators, and special actuators.

As further detailed below, in certain embodiments, the dispensing device is adequate to dispense about 100 µl of a pharmaceutical composition per actuation, wherein a single actuation dispenses about 665 mcg of olopatadine hydrochloride and about 25 mcg or about 50 mcg of mometasone furoate, preferably 25 mcg mometasone furoate.

Pharmaceutical Composition

The pharmaceutical composition for nasal administration to a human can comprise about 0.001% w/w to about 0.075% w/w mometasone, an ester thereof (e.g., mometasone furoate), or a salt thereof and about 0.5% w/w to about 0.8% w/w olopatadine or its salt (e.g., olopatadine hydrochloride). The pharmaceutical composition is stable and typically includes a fixed dose of mometasone, an ester thereof (e.g., mometasone furoate), or a salt thereof and olopatadine or its salt (e.g., olopatadine hydrochloride).

The pharmaceutical composition may be in the form of a solution or a suspension. In one preferred embodiment, the composition is in the form of a suspension (such as a single phase suspension), wherein mometasone, an ester thereof (e.g., mometasone furoate), or a salt thereof is present in particle form and olopatadine or its salt (e.g., olopatadine hydrochloride) is present in dissolved form. The mometasone, an ester thereof (e.g., mometasone furoate), or a salt thereof and olopatadine or its salt (e.g., olopatadine hydrochloride) may be present at a weight ratio of about 1:3 to about 1:106, or from about 1:5 to about 1:53 or preferably from about 1:5 to about 1:36.

The composition preferably also includes a hydrocolloid. In one embodiment, the composition is a suspension and includes a hydrocolloid in a sufficient amount to prevent phase separation (i.e., separation of the particles and solution) after 3 or 6 months of storage at 25±2° C. and 60%±5% relative humidity (RH) or at 40±2° C. and 75%±5% RH. In one embodiment, the aqueous pharmaceutical composition is a single phase suspension which remains a single phase suspension even after 3 or 6 months of storage at 25±2° C. and 60%±5% RH or at 4±2° C. and 75%±5% RH.

The term 'stable' as used in connection with aqueous suspensions refers to a composition when shaken and then stored for at least 24 hours at ambient condition does not show phase separation on visual inspection. Preferably, such stable composition does not show phase separation for a period of at least 3 days, or at least 5 days, or at least 7 days. In one aspect, the 'stable' composition shows, upon shaking (e.g., for 1 minute) and visual inspection, no lump formation and a total impurity content of no more than 1.0% after storage at ambient conditions (at about 25° C. and a relative humidity of about 60%) for a period of at least 6 months.

The drug content and impurities can be determined by various analytical techniques such as HPLC, LC-MS, and TLC.

It was observed that when various pharmaceutical compositions for nasal administration comprising mometasone, an ester thereof, or a salt thereof and olopatadine or its salt were prepared, the compositions generally showed physical separation in the suspension composition. This physical instability further leads to lack of dose uniformity. Surprisingly, it was found that addition of a hydrocolloid at certain concentrations (e.g. at a concentration of at least about 0.1% w/w) in the suspension composition yielded a physically stable composition (with no separation) suitable for nasal administration.

In another embodiment, the pharmaceutical composition is a stable fixed dose, aqueous pharmaceutical suspension composition for nasal administration to a human, where the composition comprises about 0.025% w/w to about 0.05% w/w mometasone, an ester thereof (e.g., mometasone furoate), or a salt thereof, about 0.6% w/w to about 0.7% w/w olopatadine or its salt (e.g., olopatadine hydrochloride) and a hydrocolloid.

In yet another embodiment, the pharmaceutical composition is a stable fixed dose, aqueous pharmaceutical suspension composition for nasal administration to a human, where the composition comprises about 0.025% w/w to about 0.05% w/w mometasone, an ester thereof (e.g., mometasone furoate), or a salt thereof, about 0.6% w/w to about 0.7% w/w olopatadine or its salt (e.g., olopatadine hydrochloride) and a hydrocolloid which includes carboxymethylcellulose sodium and xanthan gum. The hydrocolloid may be present at a concentration of at least about 0.1% w/w of the composition.

In yet another embodiment, the pharmaceutical composition is a stable fixed dose, aqueous pharmaceutical suspension composition for nasal administration to a human, comprising about 0.025% w/w to about 0.05% w/w mometasone furoate, about 0.6% w/w to about 0.7% w/w olopatadine hydrochloride and a hydrocolloid which comprises xanthan gum. The xanthan gum may be present at a concentration of at least about 0.1% w/w, or preferably between about 0.3% w/w to about 3% w/w of the composition.

In yet another embodiment, the pharmaceutical composition is a stable fixed dose, aqueous pharmaceutical suspension composition for nasal administration to a human, comprising about 0.025% w/w to about 0.05% w/w mometasone furoate, about 0.6% w/w to about 0.7% w/w olopatadine hydrochloride and a hydrocolloid which comprises sodium carboxymethyl cellulose. The sodium carboxymethyl cellulose may be present at a concentration of at least about 0.1% w/w, or preferably between about 0.1% w/w to about 3% w/w of the composition.

In yet another embodiment, the pharmaceutical composition is a stable fixed dose aqueous pharmaceutical composition in the form of suspension for nasal administration to a human, comprising mometasone, an ester thereof, or a pharmaceutically acceptable salt thereof (e.g., mometasone furoate), olopatadine or its pharmaceutically acceptable salt (e.g., olopatadine hydrochloride), a hydrocolloid (e.g., at a concentration of at least about 0.1% w/w of the composition) and a pharmaceutical acceptable excipient.

It will also be appreciated to the skilled artisan that in order to improve the physical properties, appearances, or smells of the composition of the present invention, one or more further pharmaceutically acceptable excipients may be added as desired. Suitable pharmaceutical acceptable excipients include, but are not limited to, chelating agents, preservatives, buffers, surfactants, isotonicity agents, taste masking agents, antioxidants, humectants, pH adjusting agents, and any combination of any of the foregoing.

Suitable surfactants which can be used for preparing aqueous nasal spray composition may include one or more of anionic, cationic, non-ionic or zwitterionic surfactants. Examples of suitable surfactants which can be employed in the aqueous nasal spray suspension may be selected from, but not limited to, polyethoxylated sorbitan derivatives such as polysorbates, their ether ethoxylates, produced by reaction of sorbitan esters with ethylene oxide, polyoxyethylene alkyl phenol, polyoxyethylene cetyl ether, polyoxyethylene alkyl-aryl ether, polyoxyethylene monolaurate, polyoxyethylene vegetable oil, polyoxyethylene sorbitan monolaurate, polyoxyethylene esters or mixed fatty and resin acids, polyoxyethylene sorbitol lanolin derivative, polyoxyethylene tridecylether, polyoxyethylene sorbitan esters of mixed fatty and resin acids, polyoxyethylene sorbitan monostearate, polyoxyethylene sorbitan monooleate, polyoxyethylene monostearate, polyoxyethylene stearyl ether, polyoxyethylene oleyl ether, polyoxyethylene tridecyl ether, polyoxyethylene fatty alcohol, polyoxyethylene alkyl amine, polyoxyethylene glycol monopalmitate, polyoxyethylene sorbitan monopalmitate, polyoxyethylene cetyl ether, polyoxyethylene oxypropylene stearate, polyoxyethylene lauryl ether, polyoxyethylene lanolin derivative, sodium oleate, quaternary ammonium derivative, potassium oleate, N-cetyl N-ethyl morpholinium ethosulfate, sodium lauryl sulfate or mixtures thereof. Preferred surfactants are polyethoxylated sorbitan derivatives (such as polysorbate 80). The amount of surfactant may range from about 0.001% to about 1% w/w relative to the total weight of the composition.

In order to improve the ability of the aqueous nasal spray suspension to be tolerated on administration to the nasal mucous membrane, it is advantageous to formulate it as isotonic. The osmolality can be set by variation of the amounts of the substances present in the aqueous nasal spray suspension besides mometasone, olopatadine and any further substances present, and/or by addition of an isotonicity agent, preferably a physiologically tolerated salt, such as, for example, sodium chloride or potassium chloride, or a physiologically tolerated polyol, such as, for example, a sugar alcohol, in particular sorbitol or glycerol, in the concentration necessary for rendering isotonic.

Examples of suitable preservatives which can be employed in the aqueous nasal spray suspension include, but are not limited to, benzyl alcohol, quaternary ammonium halides, phenylcarbinol, thimerosal, and disodium edetate. Quaternary ammonium halide preservatives are preferred. Suitable quaternary ammonium halide preservatives include polyquaternium-1 and benzalkonium halides. Preferred benzalkonium halides include benzalkonium chloride and benzalkonium bromide. The amount of the preservative present in the aqueous nasal spray suspension may range from about 0.005 to about 0.2% w/w relative to the total weight of the composition. Preferably, the preservative is present at a concentration of about 0.02% w/w relative to the total weight of the composition.

Examples of suitable chelating agents which can be employed in the aqueous nasal spray suspension include, but are not limited to, edetate disodium (EDTA), edetate trisodium, edetate tetrasodium, and diethyleneamine pentaacetate, preferably EDTA. The amount of the chelating agent present in the aqueous nasal spray suspension of the present invention may range from about 0.0002% w/w to about 0.5% w/w relative to the total weight of the composition.

Examples of suitable buffers which can be employed in the aqueous nasal spray suspension include, but are not limited to, citric acid, acetic acid, fumaric acid, hydrochloric acid, malic acid, nitric acid, phosphoric acid, propionic acid, sulfuric acid, tartaric acid, phosphate salts (e.g., dibasic sodium phosphate, such as dibasic sodium phosphate heptahydrate), or combinations thereof. The suspension of the present invention may comprise an amount of a buffer sufficient to maintain the pH of the composition to from about 3 to about 6. Preferably, the amount of buffer ranges from about 0.005% to about 1% w/w relative to the total weight of the composition.

Examples of suitable sweetener/taste masking agents which can be employed in the aqueous nasal spray suspension include, but are not limited to, sucralose, thaumatin, sucrose, saccharin (including salt forms such as sodium and calcium salts), fructose, glucose, dextrose, corn syrup, aspartame, acesulfame-K, xylitol, sorbitol, erythritol, ammonium glycyrrhizinate, neotame, mannitol, eucalyptus oil, camphor, and natural or artificial flavors or flavoring agents (for example menthol, mints, vanilla, orange, etc.), or combinations of two or more of such agents. A particularly preferred taste masking agent is sucralose. The amount of the sweetener/taste masking agent present in the aqueous nasal spray suspension may range from about 0.01% to about 1% w/w relative to the total weight of the composition.

Examples of suitable antioxidants which can be employed in the aqueous nasal spray suspension include, but are not limited to, ascorbic acid, alpha-tocopherol (vitamin-E), butylated hydroxyanisole, butylated hydroxytoluene, glutathione, and any combination of any of the foregoing. The amount of the antioxidants present in the aqueous nasal spray composition may range from about 0.0002% to about 0.5% w/w relative to the total weight of the composition.

Examples of suitable humectants which can be employed in the aqueous nasal spray suspension include, but are not limited to, glycerin, sorbitol, polyethylene glycol, propylene glycol or mixtures thereof, which are mixed with a suitable humectant vehicle such as water. The amount of humectant present in the aqueous nasal spray suspension may range from about 0.0002% to about 0.5% w/w relative to the total weight of the composition.

Suitable pH adjusting agents include, but are not limited to, sodium hydroxide and hydrochloric acid.

The pharmaceutical composition for nasal administration may have a pH of between about 3.3 and about 4.1, or between about 3.5 and about 3.9. The inventors discovered that the olopatadine hydrochloride crystallizes out of the fixed dose combination aqueous suspension at a pH of 5 to 5.5. The olopatadine hydrochloride, however, remains dissolved in the aqueous suspension at a pH of about 3.3 to about 4.1.

The aqueous pharmaceutical composition preferably is substantially free of crystals of olopatadine hydrochloride. In one embodiment, the aqueous pharmaceutical composition contains less than 2%, less than 1%, less than 0.5%, less than 0.2%, or less than 0.1% of crystalline olopatadine hydrochloride, based on the 100% total weight of olopatadine hydrochloride in the composition. In another embodiment, the aqueous pharmaceutical composition is substantially free of crystals of olopatadine hydrochloride after 3 or 6 months of storage at 25±2° C. and 60%±5% RH or at 40±2° C. and 75%±5% RH. In yet another embodiment, the aqueous pharmaceutical composition contains less than 2%, less than 1%, less than 0.5%, less than 0.2%, or less than 0.1% of crystalline olopatadine hydrochloride, based on the 100% total weight of olopatadine hydrochloride in the composition, after 3 or 6 months of storage at 25±2° C. and 60%±5% RH or at 40±2° C. and 75%±5% RH.

The osmolality of the composition may range between about 200 mOsm/kg and about 400 mOsm/kg, or about 250 mOsm/kg and about 350 mOsm/kg. The viscosity of the composition may be about 10 cps to about 200 cps or preferably from about 20 cps to about 150 cps. The viscosity can be determined by various known instruments such as a Dynamic stress rheometer or Brookfield viscometer. In a preferred embodiment, the viscosity is determined by a Brookfield viscometer by measuring torque transmission through a sample using a rotating spindle.

In yet another aspect, the pharmaceutical composition in the form of a suspension and contains mometasone, an ester thereof, or a salt thereof, preferably mometasone furoate, in particles having a mean particle size in the range of from about 1 μm to about 20 μm, or preferably from about 1 μm to about 15 μm. In an aspect, the suspension pharmaceutical composition has a mean particle size of less than 15 μm when determined by microscopy technique.

In yet another aspect, the pharmaceutical composition, when delivered as in the dispensing device can have a spray pattern having a longest axis of about 15-75 mm, a shortest axis of about 10-65 mm, and an ellipticity of about 1-2.

In another embodiment, the pharmaceutical composition is a stable fixed dose, aqueous pharmaceutical composition for nasal administration to a human, where the composition comprises about 0.001% w/w to about 0.075% w/w mometasone furoate monohydrate and about 0.5% w/w to about 0.8% w/w olopatadine hydrochloride.

In yet another embodiment, the pharmaceutical composition is a stable fixed dose pharmaceutical composition in the form of suspension for nasal administration to a human, comprising mometasone furoate monohydrate, olopatadine hydrochloride and a hydrocolloid which comprises xanthan gum at a concentration of about 0.3% w/w of the composition, wherein the composition has a pH between about 3.5 and about 3.9.

In yet another embodiment, the pharmaceutical composition is a stable fixed dose pharmaceutical composition in the form of suspension for nasal administration to a human, comprising mometasone furoate monohydrate, olopatadine hydrochloride and a hydrocolloid which comprises sodium carboxymethyl cellulose at a concentration of about 0.5% w/w of the composition, wherein the composition has a pH between about 3.5 and about 3.9.

In yet another embodiment, the pharmaceutical composition is a stable fixed dose pharmaceutical aqueous suspension composition for nasal administration to a human, where the composition comprises (1) about 0.025% w/w mometasone furoate monohydrate, (2) about 0.665% w/w olopatadine hydrochloride, (3) a hydrocolloid selected from about 0.3% w/w of xanthan gum and about 0.5% w/w carboxymethyl cellulose sodium, (4) about 0.02% w/w benzalkonium chloride, (5) about 0.4% w/w sodium chloride. (6) about 0.01% w/w di-sodium edetate, (7) about 0.94% w/w sodium phosphate heptahydrate, and (8) about 0.01% w/w polysorbate 80.

In yet another embodiment, the pharmaceutical composition is a stable fixed dose pharmaceutical aqueous suspension composition for nasal administration to a human, where the composition comprises (1) about 0.050% w/w mometasone furoate monohydrate, (2) about 0.665% w/w olopatadine hydrochloride, (3) a hydrocolloid selected from about 0.3% w/w of xanthan gum and about 0.5% w/w carboxymethyl cellulose sodium, (4) about 0.02% w/w benzalkonium chloride, (5) about 0.4% w/w sodium chloride. (6) about 0.01% w/w di-sodium edetate, (7) about 0.94% w/w sodium phosphate heptahydrate, and (8) about 0.01% w/w polysorbate 80.

In yet another embodiment, the pharmaceutical composition is a stable fixed dose pharmaceutical aqueous suspension composition for nasal administration to a human, where the composition comprises (1) about 0.025% w/w mometasone furoate monohydrate, (2) about 0.665% w/w olopatadine hydrochloride, (3) a hydrocolloid selected from about 0.3% w/w of xanthan gum and about 0.5% w/w carboxymethyl cellulose sodium, (4) about 1% w/w to about 1.2% w/w mixture of microcrystalline cellulose and carboxymethyl cellulose sodium, (5) about 0.02% w/w benzalkonium chloride, (6) about 0.4% w/w sodium chloride, (7) about 0.01% w/w di-sodium edetate, (8) about 0.94% w/w sodium phosphate heptahydrate, and (9) about 0.01% w/w polysorbate 80.

In yet another embodiment, the pharmaceutical composition is a stable fixed dose pharmaceutical aqueous suspension composition for nasal administration to a human, where the composition comprises (1) about 0.050% w/w mometasone furoate monohydrate, (2) about 0.665% w/w olopatadine hydrochloride, (3) a hydrocolloid selected from about 0.3% w/w of xanthan gum and about 0.5% w/w carboxymethyl cellulose sodium, (4) about 1% w/w to about 1.2% w/w mixture of microcrystalline cellulose and carboxymethyl cellulose sodium, (5) about 0.02% w/w benzalkonium chloride, (6) about 0.4% w/w sodium chloride, (7) about 0.01% w/w di-sodium edetate, (8) about 0.94% w/w sodium phosphate heptahydrate, and (9) about 0.01% w/w polysorbate 80.

In yet another embodiment, the pharmaceutical composition is a stable suspension suitable for nasal administration to a human, comprising (a) an aqueous solvent. (b) particles of mometasone furoate suspended in the solvent, the particles having a mean particle size of from about 1 to about 20 μm, (c) olopatadine hydrochloride dissolved in the solvent, and (d) a hydrocolloid, the suspension having a viscosity in the range of about 20 cps to about 150 cps. In one preferred embodiment, the suspension has a pH of about 3.5-3.9, and osmolality in the range of about 250 mOsm/kg to about 350 mOsm/kg. In one embodiment, the suspension further comprises a chelating agent, a preservative, a buffer, a surfactant, an isotonicity agent, and optionally a pH adjusting agent.

Preferably, the suspensions have only one phase (i.e., they are preferably a single phase suspension).

In a further embodiment, the dispensing device containing the pharmaceutical composition is provided in a kit with of a package insert containing instructions about the use of the pharmaceutical composition.

In a further embodiment, the pharmaceutical composition when dispensed from the dispensing device can provide a spray pattern having a longest axis of 15-75 mm, a shortest axis of 10-65 mm, and an ellipticity of 1-2. The spray pattern can be determined by various known techniques such as with an ADSA with NSPUA set up (Innova System) and the spray droplet size distribution can be determined by various known techniques such as with a Malvern Spraytec with NSPUA set up (Innova System).

The following describes a typical procedure for characterizing droplet size distribution of the spray. The sprayer is loaded with a composition as described above and primed by an actuating pump via an actuator until a fine mist appears out of the nozzle of the sprayer. A commercially available laser diffraction instrument is arranged so that the nozzle is about 3 cm or 6 cm below the laser beam of the laser diffraction instrument. The pump is actuated with an actuator using a constant force. The resulting spray of the composition crosses the laser beam. Data are collected for $D_{10}$, $D_{50}$, $D^{90}$, SPAN, and % Volume <10 μm. The average values for each of these parameters for three sprays are calculated.

The pharmaceutical composition may be administered with the dispensing device to treat rhinitis. In one embodiment, each spray provides (i) mometasone furoate monohydrate equivalent to about 25 mcg of mometasone furoate and (ii) olopatadine hydrochloride equivalent to about 600 mcg olopatadine (e.g., 665 mcg olopatadine hydrochloride). In one preferred embodiment, a human subject suffering from allergic rhinitis is administered two sprays of the pharmaceutical composition from the dispensing device twice daily. In another embodiment, a human subject suffering from allergic rhinitis is nasally administered 100 mcg of mometasone furoate and 1330 mcg olopatadine hydrochloride twice daily with the dispensing device. In yet another embodiment, a human subject suffering from allergic rhinitis is nasally administered 200 mcg of mometasone furoate and 2660 mcg olopatadine hydrochloride daily with the dispensing device. Rhinitis includes, but is not limited to, irritation and inflammation of the mucous membrane inside the nose and nasal and non-nasal symptoms associated therewith. It includes allergic rhinitis, persistent rhinitis, perennial rhinitis, seasonal rhinitis, chronic rhinitis, rhinitis medicamentosa, vasomotor rhinitis, infective rhinitis, autonomic rhinitis, hormonal rhinitis, drug-induced rhinitis, atrophic rhinitis, and gustatory rhinitis. Preferably, it includes allergic rhinitis, perennial rhinitis, persistent rhinitis, seasonal rhinitis and nasal and non-nasal symptoms associated therewith.

The nasal and non-nasal symptoms associated with allergic rhinitis include sneezing, nasal itching, rhinorrhea (runny nose), nasal obstruction, coughing, ocular pruritis, excess lacrimation, headache, fatigue, common cold (also known as nasopharyngitis, rhinopharyngitis, acute coryza, or cold), malaise and cognitive impairment.

The pharmaceutical composition may comprise one or more additional pharmaceutical active agent(s) selected from the therapeutic category of, but not limited to, nonsteroidal anti-inflammatory agents, decongestants, and any combination of any of the foregoing.

In one aspect, the pharmaceutical composition includes about 0.001% w/w to about 0.075% w/w mometasone, an ester thereof (e.g., mometasone furoate), or a salt thereof in particulate form and about 0.5% w/w to about 0.8% w/w olopatadine or its salt (e.g., olopatadine hydrochloride) in dissolved form. In this aspect, the composition could further include a hydrocolloid system, for example, in an amount sufficient to inhibit phase separation for at least 24 hours when stored at 25±2° C. and 60%±5% relative humidity. In one embodiment, the composition when stored for up to 12 months at 25±2° C. and 60%±5% relative humidity in the dispensing device contains has one or more of the following properties:

(i) the composition contains not more than 1% of total impurities (after storage);

(ii) the composition contains not more than 1% of DMC (after storage);

(iii) the composition contains not more than 1% of DMCF (after storage);

(iv) the composition contains not more than 1% of α-hydroxy olopatadine (after storage);

(v) the composition contains not more than 1% of olopatadine E-isomer (after storage);

(vi) the composition contains not more than 1% of Olopatadine Related Compound B (after storage); and/or (vii) the composition contains not more than 0.42% of other impurities of olopatadine (after storage).

Methods of Treatment

The inventors have also surprisingly found that nasal administration of a pharmaceutical composition of mometasone, an ester thereof (e.g., mometasone furoate), or a salt thereof and olopatadine or a salt thereof (such as olopatadine hydrochloride) provides a faster onset of action of relief of symptoms associated with allergic rhinitis, such as seasonal allergic rhinitis or perennial allergic rhinitis, when compared to olopatadine hydrochloride monotherapy or mometasone fuorate monotherapy. In particular, the pharmaceutical composition provides faster relief of nasal symptoms, such as nasal congestion, rhinorrhea, itching and sneezing. The pharmaceutical composition may also provide a faster onset of action of ocular symptoms, such as ocular itching, tearing/watery eyes and ocular redness. The onset of action may be less than 30 minutes, such as within about 15 minutes, such as within about 10 minutes. One embodiment is a method of treating allergic rhinitis in a subject (e.g., a human) in need thereof comprising nasally administering to the subject an effective amount of a fixed-dose pharmaceutical composition, such as from a dispensing device described above, where the pharmaceutical composition comprises mometasone, an ester thereof, or a salt thereof and olopatadine or its salt. Preferably, the composition is nasally administered as 1 or 2 sprays per nostril of the subject at least once daily. Each spray preferably comprises mometasone, an ester thereof, or a salt thereof and olopatadine or its salt in a weight ratio of about 1:5 to about 1:60, such as in a weight ratio of from about 1:12 to about 1:53 from about 1:13.3 to about 1:50, or from about 1:18 to about 1:40 (based on the equivalent weight of olopatadine free base). In one particular embodiment, the fixed-dose pharmaceutical composition is a suspension wherein the mometasone, an ester thereof, or a salt thereof is present in particulate form and the olopatadine or its salt is present in dissolved form.

Yet another embodiment is a method for providing faster onset of relief of symptoms associated with allergic rhinitis in a human subject in need thereof comprising nasally administering twice daily, two sprays per nostril of a fixed-dose pharmaceutical composition, such as from a dispensing device described above, where the pharmaceutical composition comprises mometasone, an ester thereof, or a salt thereof (e.g., mometasone furoate) and olopatadine its salt (e.g., olopatadine hydrochloride). This method may provide faster onset of relief of one or more symptoms compared to administration of the mometasone, an ester thereof, or a salt thereof alone or olopatadine or its salt alone. Each spray may comprise mometasone, an ester thereof, or a salt thereof and olopatadine or its salt in a weight ratio of about 1:5 to about 1:60 (such as a weight ratio of about 1:12 to about 1:53, about 1:13.3 to about 1:50, or from about 1:18 to about 1:40) (based on the equivalent weight of olopatadine free base) (for example, each spray comprises about 12.5 mcg, about 25 mcg, about 37.5 mcg, about 50 mcg, or about 62.5 mcg of mometasone, an ester thereof, or a salt thereof (such as about 50 mcg mometasone furoate) and olopatadine hydrochloride equivalent to about 300 mcg, about 450 mcg, about 600 mcg, about 750 mcg, or about 900 mcg of olopatadine (such as about 665 mcg olopatadine hydrochloride)). The administration may provide relief from one or more symptoms within 30 minutes, such as within 15 minutes or 10 minutes. In another embodiment, the administration may provide relief from one or more symptoms of allergic rhinitis (such as nasal symptoms) in a subject exposed to an environmental exposure chamber (EEC) (such as one with ragweed pollen at a concentration of 3500±500 particles/m3 for 6 hours) in less than 15 minutes, such as within about 10 minutes.

In one embodiment, the methods herein provide faster onset of action for relief of nasal symptoms in the subject. In another embodiment, the methods herein provide faster onset of action for relief of ocular symptoms in the subject.

In one embodiment, the pharmaceutical composition provides faster onset of action for relief of nasal symptoms in the subject. In another embodiment, the pharmaceutical composition provides faster onset of action for relief of ocular symptoms in the subject.

Yet another embodiment is a method of treating a human subject suffering from allergic rhinitis comprising the step of administering to the subject a pharmaceutical composition for twice daily nasal administration of two sprays per nostril, such as from a dispensing device described above, wherein (i) the pharmaceutical composition provides an onset of action within 15 minutes for the treatment of allergic rhinitis and (ii) each spray of the pharmaceutical composition comprises about 25 mcg of mometasone furoate and about 665 mcg of olopatadine hydrochloride.

Yet another embodiment is a method of treating a human subject suffering from allergic rhinitis comprising the steps of:

(a) prescribing to a subject (e.g., a human subject) a fixed-dose pharmaceutical composition for twice daily nasal administration of two sprays per nostril, optionally in combination with a dispensing device described above, wherein the fixed-dose pharmaceutical composition comprises mometasone, an ester thereof, or a salt thereof (such as mometasone furoate) and olopatadine or its salt (such as olopatadine hydrochloride), and each spray comprises mometasone, an ester thereof, or a salt thereof and olopatadine or its salt in a weight ratio of about 1:5 to about 1:60 (such as a weight ratio of about 1:12 to about 1:53, about 1:13.3 to about 1:50, or from about 1:18 to about 1:40) (based on the equivalent weight of olopatadine free base) (for example, each spray comprises about 12.5 mcg, about 25 mcg, about 37.5 mcg, about 50 mcg, or about 62.5 mcg of mometasone, an ester thereof, or a salt thereof (such as about 50 mcg mometasone furoate) and olopatadine hydrochloride equivalent to about 300 mcg, about 450 mcg, about 600 mcg, about 750 mcg, or about 900 mcg of olopatadine (such as about 665 mcg olopatadine hydrochloride)), the prescribing being performed in response to (i) marketing of the pharmaceutical composition, optionally in combination with a dispensing device described above, as (A) providing faster onset of action (such as an onset of action within less than 30 minutes, such as within 15 minutes, such as within 10 minutes) for relief of one or more symptoms (e.g., nasal symptoms) of allergic rhinitis than nasal administration of mometasone, an ester thereof, or a salt thereof (such as 25 or 50 mcg mometasone furoate) or olopatadine or its salt (such as 665 mcg olopatadine hydrochloride) alone, (B) providing relief of one or more symptoms of allergic rhinitis within 15 minutes (or 30 minutes). (C) providing faster onset of action (such as within 15 minutes, such as within about 10 minutes) for relief of one or more symptoms (e.g., nasal symptoms) of allergic rhinitis in subjects exposed to an environmental exposure chamber (EEC) (such as one with ragweed pollen at a concentration of 3500±500 particles/m$^3$ for 6 hours) than nasal administration of the mometasone, an ester thereof, or a salt thereof or the olopatadine or its salt alone, and/or (D) providing relief from one or more symptoms of allergic rhinitis (such as nasal symptoms) in subjects exposed to an environmental exposure chamber (EEC) (such as one with ragweed pollen at a concentration of 3500±500 particles/m$^3$ for 6 hours) within 15 minutes, such as within about 10 minutes, and (ii) diagnosis of the human subject as suffering from allergic rhinitis; and (b) administering the prescribed pharmaceutical composition, optionally with a dispensing device described above, to the subject. In one preferred embodiment, each spray of the fixed-dose pharmaceutical composition provides 25 mcg mometasone furoate and 665 mcg olopatadine hydrochloride.

Yet another embodiment is a method of treating a human subject suffering from allergic rhinitis (such as seasonal allergic rhinitis or perennial allergic rhinitis) comprising the step of administering to the subject a prescribed fixed-dose pharmaceutical composition for twice daily nasal administration of two sprays per nostril, optionally with a dispensing device described above, where the fixed-dose pharmaceutical composition comprises mometasone, an ester thereof, or a salt thereof (such as mometasone furoate) and olopatadine or its salt (such as olopatadine hydrochloride), and each spray comprises mometasone, an ester thereof, or a salt thereof and olopatadine or its salt in a weight ratio of about 1:5 to about 1:60 (such as a weight ratio of about 1:12 to about 1:53, about 1:13.3 to about 1:50, or from about 1:18 to about 1:40) (based on the equivalent weight of olopatadine free base) (for example, each spray comprises about 12.5 mcg, about 25 mcg, about 37.5 mcg, about 50 mcg, or about 62.5 mcg of mometasone, an ester thereof, or a salt thereof (such as about 50 mcg mometasone furoate) and olopatadine hydrochloride equivalent to about 300 mcg, about 450 mcg, about 600 mcg, about 750 mcg, or about 900 mcg of olopatadine (such as about 665 mcg olopatadine hydrochloride)). The pharmaceutical composition is prescribed in response to (a) marketing of the pharmaceutical composition, optionally with a dispensing device described above, as (A) providing faster onset of action (such as an onset of action within less than 30 minutes, such as within 15 minutes, such as within 10 minutes) for relief of symptoms (e.g., nasal symptoms) of allergic rhinitis than nasal administration of mometasone, an ester thereof, or a salt thereof (such as 50 mcg mometasone furoate) or olopatadine or its salt (such as 665 mcg olopatadine hydrochloride) alone or (B) providing relief of one or more symptoms of allergic rhinitis within 15 minutes (or 30 minutes), and (b) a diagnosis of the subject as suffering from allergic rhinitis. In one preferred embodiment, each spray of the fixed-dose pharmaceutical composition provides 25 mcg mometasone furoate and 665 mcg olopatadine hydrochloride.

The administration of the pharmaceutical composition, such as with a dispensing device described above, may provide relief from one or more symptoms of allergic rhinitis (such as nasal symptoms or ocular symptoms) in a subject faster (e.g., an onset of action in less than 30 minutes, such as within about 15 minutes, such as within 10 minutes) than nasal administration of the mometasone, an ester thereof, or a salt thereof or the olopatadine or its salt alone. In another embodiment, the administration may provide relief from one or more symptoms of allergic rhinitis (such as nasal symptoms) in a subject exposed to an environmental exposure chamber (EEC) (such as one with ragweed pollen at a concentration of 3500±500 particles/m3 for 6 hours) faster (e.g., an onset of action in less than 15 minutes, such as within about 10 minutes) than nasal administration of the mometasone, an ester thereof, or a salt thereof or the olopatadine or its salt alone.

Yet another embodiment is a method for providing faster onset of relief of symptoms associated with allergic rhinitis in a human subject in need thereof comprising nasally administering twice daily, two sprays per nostril of a fixed-dose pharmaceutical composition, such as with a dispensing device described above, where the pharmaceutical composition comprises mometasone, an ester thereof, or a salt thereof (e.g., mometasone furoate) and olopatadine its salt (e.g., olopatadine hydrochloride). This method may provide faster onset of relief of one or more symptoms compared to administration of the mometasone, an ester thereof, or a salt thereof alone or olopatadine or its salt alone. Each spray may comprise mometasone, an ester thereof, or a salt thereof and olopatadine or its salt in a weight ratio of about 1:5 to about 1:60 (such as a weight ratio of about 1:12 to about 1:53, about 1:13.3 to about 1:50, or from about 1:18 to about 1:40) (based on the equivalent weight of olopatadine free base) (for example, each spray comprises about 12.5 mcg, about 25 mcg, about 37.5 mcg, about 50 mcg, or about 62.5 mcg of mometasone, an ester thereof, or a salt thereof (such as about 50 mcg mometasone furoate) and olopatadine hydrochloride equivalent to about 300 mcg, about 450 mcg, about 600 mcg, about 750 mcg, or about 900 mcg of olopatadine (such as about 665 mcg olopatadine hydrochloride)). The administration may provide relief from one or more symptoms within 30 minutes, such as within 15 minutes or within 10 minutes. In another embodiment, the administration may provide relief from one or more symptoms of allergic rhinitis (such as nasal symptoms) in a subject exposed to an environmental exposure chamber (EEC) (such as one with ragweed pollen at a concentration of 3500±500 particles/m$^3$ for 6 hours) in less than 15 minutes, such as within about 10 minutes.

Yet another embodiment is a method of treating a human subject suffering from allergic rhinitis comprising the step of administering to the subject a pharmaceutical composition for twice daily nasal administration of two sprays per nostril, such as with a dispensing device described above, wherein (i) the pharmaceutical composition provides an onset of action within 15 minutes for the treatment of allergic rhinitis and (ii) each spray of the pharmaceutical composition comprises about 25 mcg of mometasone furoate and about 665 mcg of olopatadine hydrochloride.

In one embodiment of any of the methods described herein, the allergic rhinitis is selected from perennial allergic rhinitis, persistent allergic rhinitis, seasonal allergic rhinitis, and nasal and/or non-nasal symptoms associated therewith. In one preferred embodiment, of any of the methods described herein, the allergic rhinitis is seasonal allergic rhinitis. In another preferred embodiment, of any of the methods described herein, the allergic rhinitis is perennial allergic rhinitis.

It will be understood that various modifications may be made to the embodiments disclosed herein. Therefore the above description should not be construed as limiting, but merely as exemplifications of preferred embodiments. Other arrangements and methods may be implemented by those skilled in the art without departing from the scope and spirit of this invention.

The following examples are provided to enable one skilled in the art to practice the invention and are merely illustrative of the invention. The examples should not be read as limiting the scope of the invention.

EXAMPLES

Examples 1 and 2

Suspension Compositions Containing Mometasone Furoate, Olopatadine HCl and Carboxymethylcellulose Sodium

| SN | Ingredient | Example 1 (% w/w) | Example 2 (% w/w) |
|---|---|---|---|
| 1 | Mometasone Furoate monohydrate Eq. to Mometasone furoate | 0.050 | 0.025 |
| 2 | Olopatadine Hydrochloride | 0.665 | 0.665 |
| 3 | Avicel RC 591 (Microcrystalline Cellulose and Carboxymethylcellulose Sodium) | 1.200 | 1.200 |
| 4 | Benzalkonium chloride (50% solution) | 0.040 | 0.040 |
| 5 | Carboxymethylcellulose Sodium (Cekol 2000 P) | 0.500 | 0.500 |
| 6 | Sodium chloride | 0.410 | 0.410 |
| 7 | Edetate disodium | 0.010 | 0.010 |
| 8 | Dibasic sodium phosphate heptahydrate | 0.940 | 0.940 |
| 9 | Polysorbate 80 | 0.010 | 0.010 |
| 10 | Sodium Hydroxide | Q.S. | Q.S. |
| 11 | Hydrochloric acid | Q.S. | Q.S. |
| 12 | Water for injection | Q.S. | Q.S. |
| Observations | | | |
| Physical observation on standing for 24 hours | | No phase separation observed | No phase separation observed |
| Mean Particle size by microscopy | | Below 15 μm. | Below 15 μm. |

Manufacturing Procedure:
1. Avicel RC-591 was added in water for injection with homogenization and allowed to hydrate.
2. Carboxymethylcellulose Sodium was dispersed in water for injection and added to step-1.
3. Dibasic sodium phosphate heptahydrate. Sodium chloride, Edetate disodium and Olopatadine were dissolved in water. The pH was adjusted to 2.8-3.2 with Hydrochloric acid.
4. Step-3 was added to Step-1 with homogenization.
5. Polysorbate 80 was dissolved in water for injection. Mometasone Furoate monohydrate was added and stirred to form slurry.
6. Step-5 was added to Step-4 with homogenization.
7. Benzalkonium chloride was dissolved in water for injection.
8. Step-7 was added to Step-6 with homogenization.
9. The pH was checked and adjusted to 3.5-3.9 with HCl and the total weight was adjusted with Water for injection. The osmolality of the composition was about 250-350 mOsm/kg. The composition was subjected to stability studies at different conditions.

The results of the same are as follows:
Container details: Sprayer containing HDPE bottle crimped with pump and fitted with an actuator and cap.

| | Stability Study Data | | | | | |
|---|---|---|---|---|---|---|
| | Initial | | 3 months | | 6 months | |
| Test | Ex. 1 | Ex. 2 | Ex. 1 | Ex. 2 | Ex. 1 | Ex. 2 |
| Stability condition (25° C. ± 2° C. & 60% RH ± 5% RH) | | | | | | |
| pH | | 3.61 | 3.69 | 3.73 | 3.78 | 3.81 |
| Osmolality (mOsm)* | 310 | 308 | 299 | 298 | 302 | 311 |
| Viscosity (cps)** | | 32.5 | 42.5 | 42.3 | 40.6 | 40.9 |
| Weight per ml (g/ml) | | 1.01 | 1.021 | 1.024 | 1.029 | 1.019 |
| Assay of mometasone furoate (% w/w) | 101 | 102.4 | 99.1 | 99.3 | 98.2 | 97.2 |
| Assay of olopatadine hydrochloride (% w/w) | 98.2 | 99.9 | 97.3 | 99.1 | 97.8 | 97.9 |

| | Stability Study Data | | | | | |
|---|---|---|---|---|---|---|
| | Initial | | 3 months | | 6 months | |
| Test | Ex. 1 | Ex. 2 | Ex. 1 | Ex. 2 | Ex. 1 | Ex. 2 |
| Related substances for mometasone furoate | | | | | | |
| Impurity DMCF (%) | 0.02 | 0.03 | 0.09 | 0.10 | 0.14 | 0.17 |
| Any other impurity (%) | 0.04 | | 0.04 | | 0.03 | |
| Total impurities (%) | 0.09 | | 0.23 | 0.29 | 0.31 | 0.34 |
| Related substances for olopatadine hydrochloride | | | | | | |
| Olopatadine E-isomer (%) | 0.08 | | 0.07 | 0.09 | 0.09 | |
| Any other impurity (%) | 0.03 | 0.04 | 0.09 | 0.12 | 0.11 | 0.11 |
| Total impurities (%) | 0.15 | 0.16 | 0.20 | 0.25 | 0.37 | 0.38 |
| Spray Pattern (at 6 cm) | | | | | | |
| Major Axis (mm) | 52 | | 60 | 63 | 59 | 61 |
| Minor Axis (mm) | 43 | 47 | 49 | 53 | 49 | 51 |
| Ellipticity | 1.2 | 1.1 | 1.1 | 1.2 | 1.1 | 1.2 |
| Droplet size distribution (at 6 cm) | | | | | | |
| $D_{10}$ (μm) | 18.91 | 19.45 | 19.26 | 19.70 | 19.33 | 18.88 |
| $D_{50}$ (μm) | 36.39 | 37.61 | 35.96 | 37.34 | 39.28 | 37.85 |
| $D_{90}$ (μm) | 72.46 | 76.44 | 70.29 | 75.78 | 85.42 | 72.07 |
| SPAN | 1.47 | 1.51 | 1.42 | 1.5 | 1.67 | 1.46 |
| Stability condition (40° C. ± 2° C. & 75% RH ± 5% RH) | | | | | | |
| pH | | 3.61 | 3.68 | 3.72 | 3.59 | 3.68 |
| Osmolality (mOsm) | 310 | 308 | 298 | 306 | 305 | 299 |
| Viscosity (cps) | | 32.5 | 45.2 | 42.6 | 41.8 | 41.5 |
| Weight per ml (g/ml) | | 1.01 | 1.023 | 1.019 | 1.026 | 1.025 |
| Assay of mometasone furoate (%) | 101 | 102.4 | 99.8 | 100.4 | 98.3 | 98.4 |
| Assay of oloptadine hydrochloride (%) | 98.2 | 99.9 | 99.3 | 102.5 | 98.7 | 99.7 |
| Related substances for mometasone furoate | | | | | | |
| Impurity DMCF (%) | 0.02 | 0.03 | 0.014 | 0.20 | 0.25 | 0.25 |
| Any other impurity (%) | 0.04 | 0.04 | 0.04 | 0.03 | 0.03 | 0.04 |
| Total impurities (%) | 0.09 | | 0.25 | 0.39 | 0.40 | 0.46 |
| Related substances for olopatadine hydrochloride | | | | | | |
| Olopatadine E-isomer (%) | 0.08 | | 0.07 | 0.08 | 0.08 | 0.09 |
| Any other impurity (%) | 0.03 | 0.04 | 0.21 | 0.18 | 0.31 | 0.30 |
| Total impurities (%) | 0.15 | 0.16 | 0.32 | 0.36 | 0.68 | 0.64 |
| Spray Pattern (at 6 cm) | | | | | | |
| Major Axis (mm) | 52 | 52 | 61 | 58 | 58 | 58 |
| Minor Axis (mm) | 43 | 47 | 50 | 49 | 48 | 49 |
| Ellipticity | 1.2 | 1.1 | 1.2 | 1.2 | 1.2 | 1.2 |
| Droplet size distribution (at 6 cm) | | | | | | |
| $D_{10}$ (μm) | 18.91 | 19.45 | 19.49 | 19.27 | 18.05 | 18.09 |
| $D_{50}$ (μm) | 36.39 | 37.61 | 35.29 | 34.68 | 36.19 | 36.12 |
| $D_{90}$ (μm) | 72.46 | 76.44 | 64.66 | 63.49 | 71.89 | 70.06 |
| SPAN | 1.47 | 1.51 | 1.28 | 1.27 | 1.50 | 1.44 |

*Determined by Advanced Instruments Osmometer (Model 3250).
**Determined by Brookfield viscometer.

Examples 3 and 4

Suspension Compositions Containing Mometasone Furoate, Olopatadine HCl and Xanthan Gum

| SN | Ingredient | Example 3 (% w/w) | Example 4 (% w/w) |
|---|---|---|---|
| 1 | Mometasone Furoate monohydrate Eq. to Mometasone furoate | 0.050 | 0.025 |
| 2 | Olopatadine HCl | 0.665 | 0.665 |
| 3 | Avicel RC 591 (Microcrystalline Cellulose and Carboxymethylcellulose Sodium) | 1.000 | 1.000 |
| 4 | Benzalkonium chloride (50% solution) | 0.040 | 0.040 |
| 5 | Xantural 75 (Xanthan Gum) | 0.300 | 0.300 |
| 6 | Sodium chloride | 0.410 | 0.410 |
| 7 | Edetate disodium | 0.010 | 0.010 |
| 8 | Dibasic sodium phosphate heptahydrate | 0.940 | 0.940 |
| 9 | Polysorbate 80 | 0.010 | 0.010 |
| 10 | Sodium Hydroxide | Q.S. | Q.S. |
| 11 | Hydrochloric acid | Q.S. | Q.S. |
| 12 | Water for injection | Q.S. | Q.S. |
| | Observations | | |
| | Physical observation on standing for 24 hours | No phase separation observed | No phase separation observed |
| | Mean Particle size by microscopy | Below 15 μm. | Below 15 μm. |

Manufacturing Procedure:

1. Avicel RC-591 was added in Water for injection with homogenization and allowed to hydrate.

2. Xanthan gum was dispersed in Water for injection and added to step-1.

3. Dibasic sodium phosphate heptahydrate. Sodium chloride, Edetate disodium and Olopatadine were dissolved in water. The pH was adjusted to 2.8-3.2 with Hydrochloric acid.

4. Step-3 was added to Step-1.

5. Polysorbate 80 was dissolved in water for injection. Mometasone Furoate monohydrate was added to it and stirred to form slurry.

6. Step-5 was added to Step-4 with homogenization.

7. Benzalkonium chloride was dissolved in water for injection.

8. Step-7 was added to Step-6 with homogenization.

9. The pH was checked and adjusted to 3.5-3.9 with HCl and the weight was adjusted with water for injection. The osmolality of the composition was about 250-350 mOsm/kg.

The composition was subjected to stability studies at different conditions. The results of the same are as follows:

Container details: Sprayer containing HDPE bottle crimped with pump and fitted with a actuator and cap

Stability Study Results

| | Initial | | 3 months | | 6 months | |
|---|---|---|---|---|---|---|
| Test | Ex. 3 | Ex. 4 | Ex. 3 | Ex. 4 | Ex. 3 | Ex. 4 |
| Stability condition (25° C. ± 2° C. & 60% RH ± 5% RH) | | | | | | |
| pH | 3.65 | 3.67 | 3.78 | 3.65 | 3.70 | 3.62 |
| Osmolality (mOsm) | 307 | 312 | 302 | 316 | 308 | 308 |
| Viscosity (cps) | 124.2 | 129.1 | 127.9 | 129.9 | 126.2 | 126.8 |
| Weight per ml (g/ml) | 1.019 | 1.022 | 1.02 | 1.023 | 1.02 | 1.019 |
| Assay of mometasone furoate (%) | 99.9 | 102.8 | 102.2 | 99.9 | 98.7 | 100.4 |
| Assay of olopatadine hydrochloride (%) | 99.2 | 100.7 | 99.7 | 99.7 | 99.4 | 99.6 |
| Related substances for mometasone furoate | | | | | | |
| Impurity DMCF (%) | 0.02 | 0.03 | 0.04 | 0.05 | 0.03 | 0.05 |
| Any other impurity (%) | | 0.03 | | 0.04 | 0.03 | 0.04 |
| Total impurities (%) | 0.11 | 0.10 | 0.15 | 0.16 | 0.12 | 0.16 |
| Related substances for olopatadine hydrochloride | | | | | | |
| Olopatadine E-isomer (%) | 0.08 | 0.07 | 0.09 | 0.11 | 0.11 | 0.10 |
| Any other impurity (%) | 0.03 | 0.04 | 0.05 | 0.05 | 0.08 | 0.08 |
| Total impurities (%) | 0.18 | 0.15 | 0.24 | 0.20 | 0.33 | 0.33 |
| Spray Pattern (at 6 cm) | | | | | | |
| Major Axis (mm) | 46 | | 59 | 59 | 56 | 54 |
| Minor Axis (mm) | 38 | | 47 | 44 | 35 | 43 |
| Ellipticity | 1.2 | | 1.3 | 1.4 | 1.6 | 1.3 |
| Droplet size distribution (at 6 cm) | | | | | | |
| $D_{10}$ (μm) | 21.58 | 21.03 | 20.95 | 20.27 | 18.73 | 18.34 |
| $D_{50}$ (μm) | 40.44 | 39.79 | 37.86 | 37.93 | 36.66 | 36.16 |
| $D_{90}$ (μm) | 78.25 | 77.55 | 74.07 | 74.93 | 70.63 | 70.99 |
| SPAN | 1.40 | 1.42 | 1.40 | 1.44 | 1.40 | 1.45 |

Stability Study Results

| | Initial | | 3 months | | 6 months | |
|---|---|---|---|---|---|---|
| Test | Ex. 3 | Ex. 4 | Ex. 3 | Ex. 4 | Ex. 3 | Ex. 4 |
| Stability condition (40° C. ± 2° C. & 75% RH ± 5% RH) | | | | | | |
| pH | 3.65 | 3.67 | 3.70 | 3.77 | 3.78 | 3.65 |
| Osmolality (mOsm) | 307 | 312 | 309 | 305 | 302 | 316 |
| Viscosity (cps) | 124.2 | 129.1 | 129.6 | 124.3 | 127.9 | 129.9 |
| Weight per ml (g/ml) | 1.05 | 1.022 | 1.017 | 1.027 | 1.022 | 1.020 |
| Assay of mometasone furoate (%) | 99.9 | 102.8 | 101.7 | 100.6 | 99.6 | 98.4 |
| Assay of oloptadine hydrochloride (%) | 99.2 | 100.7 | 101.7 | 99.4 | 99.7 | 99.9 |
| Related substances for mometasone furoate | | | | | | |
| Impurity DMCF (%) | 0.02 | 0.02 | 0.010 | 0.12 | 0.10 | 0.12 |
| Any other impurity (%) | 0.03 | 0.03 | 0.02 | 0.03 | 0.05 | 0.03 |
| Total impurities (%) | 0.011 | 0.10 | 0.20 | 0.22 | 0.18 | 0.21 |
| Related substances for olopatadine hydrochloride | | | | | | |
| Olopatadine E-isomer (%) | 0.08 | 0.07 | 0.12 | 0.13 | 0.11 | 0.11 |
| Any other impurity (%) | 0.03 | 0.04 | 0.06 | 0.06 | 0.12 | 0.12 |
| Total impurities (%) | 0.18 | 0.15 | 0.26 | 0.26 | 0.18 | 0.21 |
| Spray Pattern (at 6 cm) | | | | | | |
| Major Axis (mm) | 46 | 46 | 56 | 58 | 54 | 55 |
| Minor Axis (mm) | 38 | 38 | 45 | 49 | 34 | 43 |
| Ellipticity | 1.2 | 1.2 | 1.3 | 1.2 | 1.3 | 1.6 |
| Droplet size distribution (at 6 cm) | | | | | | |
| $D_{10}$ (μm) | 21.58 | 21.03 | 20.67 | 23.16 | 19.13 | 19.16 |
| $D_{50}$ (μm) | 40.44 | 39.79 | 38.06 | 39.08 | 37.34 | 37.26 |
| $D_{90}$ (μm) | 78.25 | 77.55 | 75.63 | 69.37 | 72.36 | 72.49 |
| SPAN | 1.40 | 1.42 | 1.44 | 1.19 | 1.42 | 1.43 |

Comparative Examples A and B

Suspension Composition Containing Mometasone Furoate, and Olopatadine HCl

| | | Example (% w/w) | |
|---|---|---|---|
| SN | Ingredient | A | B |
| 1 | Mometasone Furoate monohydrate Eq. to Mometasone furoate | 0.050 | 0.050 |
| 2 | Olopatadine HCl | 0.665 | 0.665 |
| 3 | Avicel RC 591 (Microcrystalline Cellulose and Carboxymethyl cellulose Sodium) | 1.00 | 1.00 |
| 4 | Benzalkonium chloride (50% solution) | 0.040 | 0.040 |
| 5 | Carboxymethylcellulose Sodium (Cekol 2000 P) | 0.00 | 0.150 |
| 6 | Sodium chloride | 0.410 | 0.410 |
| 7 | Edetate disodium | 0.010 | 0.010 |
| 8 | Dibasic sodium phosphate heptahydrate | 0.940 | 0.940 |
| 9 | Polysorbate 80 | 0.010 | 0.010 |
| 10 | Sodium Hydroxide | Q.S. | Q.S. |
| 11 | Hydrochloric acid | Q.S. | Q.S. |
| 12 | Water for injection | Q.S. | Q.S. |
| Observations | | | |
| | pH | 3.7 | 3.7 |
| | Physical observation on standing for 24 hours | Phase separation observed | Phase separation observed |

Manufacturing Procedure:

The manufacturing procedure as mentioned in Example 1 was followed.

Comparative Examples C and D

Suspension Composition Containing Mometasone Furoate and Olopatadine HCl

| | | Example (% w/w) | |
|---|---|---|---|
| SN | Ingredient | C | D |
| 1 | Mometasone Furoate monohydrate Eq. to Mometasone furoate | 0.050 | 0.050 |
| 2 | Olopatadine HCl | 0.665 | 0.665 |
| 3 | Avicel RC 591 (Microcrystalline Cellulose and Carboxymethyl cellulose Sodium) | 1.000 | 1.000 |
| 4 | Benzalkonium chloride (50% solution) | 0.040 | 0.040 |
| 5 | Xantural 75 (Xanthan Gum) | 0.00 | 0.20 |
| 6 | Sodium chloride | 0.410 | 0.410 |
| 7 | Edetate disodium | 0.010 | 0.010 |
| 8 | Dibasic sodium phosphate heptahydrate | 0.940 | 0.940 |
| 9 | Polysorbate 80 | 0.010 | 0.010 |
| 10 | Sodium Hydroxide | Q.S. | Q.S. |
| 11 | Hydrochloric acid | Q.S. | Q.S. |
| 12 | Water for injection | Q.S. | Q.S. |

-continued

| SN | Ingredient | Example (% w/w) | |
|---|---|---|---|
| | | C | D |
| | Observations | | |
| | pH | 3.73 | 3.70 |
| | Physical observation on standing for 24 hours | Phase separation observed | Phase separation observed |

Manufacturing Procedure:

The manufacturing procedure as mentioned in Example 3 was followed.

Example 5

Clinical Study of Fixed Dose Combination of Mometasone and Olopatadine Nasal Spray in Human Patients The study was a single-centre, double blind, double-dummy, randomized, parallel-group, comparative Environmental Exposure Chamber (EEC) study to evaluate the efficacy, safety and tolerability of (i) two fixed dose combination products of mometasone furoate and olopatadine hydrochloride nasal spray. (ii) a fixed dose combination of azelastine hydrochloride and fluticasone propionate nasal spray (DYMISTA®), (iii) olopatadine nasal spray (PATANASE®), and (iv) a placebo nasal spray in patients with seasonal allergic rhinitis (SAR).

Key Objectives

To evaluate the efficacy of two strengths of the fixed dose combination (FDC) of mometasone furoate and olopatadine hydrochloride nasal spray when compared with a placebo nasal spray.

To evaluate the comparative efficacy of (i) two regimens of FDC products containing mometasone furoate and olopatadine hydrochloride nasal spray, (ii) a fixed dose combination of azelastine hydrochloride and fluticasone propionate nasal spray (DYMISTA®), and (iii) Olopatadine nasal spray (PATANASE®).

To compare the efficacy of (i) a fixed dose combination of azelastine hydrochloride and fluticasone propionate nasal spray and (ii) olopatadine nasal spray, when compared with a placebo nasal spray.

To compare the onset of action between active treatments groups after the first dose defined as "the first time point after initiation of treatment when the drug demonstrates a significant reduction in instantaneous TNSS compared to the placebo treatment that proves durable from this point."

To compare the EEC-Quality of Life Questionnaire (QoLQ) and tolerability and acceptability between a fixed dose combination of mometasone furoate and olopatadine hydrochloride once daily and a fixed dose combination of mometasone furoate and olopatadine hydrochloride twice daily.

To evaluate the comparative safety between the various treatment arms.

Sample Size

A total of 36 patients per treatment arm were randomized in the study. The total number of randomized subjects throughout the five treatment arms was 180.

Patient Population

Subjects suffering from seasonal allergic rhinitis for the last two years that require treatment either with intranasal antihistamines and/or intranasal steroids were included in the study.

Key Subject Selection Criteria

1. Patients age ≥18 and ≤65 years inclusive of either sex;
2. Patient with a known clinical history of seasonal allergic rhinitis (for at least 2 years) and exhibiting a positive skin prick test (wheal diameter at least 3 mm greater than saline control) to one of the regional allergens;
3. Patients with the ability to understand and sign a written informed consent form, which must have been obtained prior to screening; and
4. Patients willing to comply with the protocol requirements.

Study Design

Patients were randomized to treatment in a 1:1:1:1:1 ratio to the following five treatment arms, at one study site:

1. Fixed dose combination of olopatadine hydrochloride 665 mcg and mometasone furoate 25 mcg twice daily (BID)
2. Fixed dose combination of olopatadine hydrochloride 665 mcg and mometasone furoate 50 mcg once daily (QD)
3. DYMISTA® nasal spray (azelastine hydrochloride 137 mcg+fluticasone propionate 50 mcg) Spray twice daily (BID)
4. PATANASE® nasal spray (olopatadine hydrochloride 665 mcg) twice daily (BID)
5. Placebo nasal spray The double-dummy design including four masked nasal spray bottles (two for evening dosing and two for morning dosing) were utilized for this study (see Table A).

TABLE A

Treatment Administration Using Four Masked Bottles of Nasal Sprays

| | | Morning | | Evening | |
|---|---|---|---|---|---|
| | Treatment Arm | 1st bottle | 2nd bottle | 1st bottle | 2nd bottle |
| 1 | TP-1: Fixed dose combination of mometasone furoate 25 mcg + olopatadine hydrochloride 665 mcg twice daily (BID) | Active | Active | Active | Active |
| 2 | TP-2: Fixed dose combination of mometasone furoate 50 mcg + olopatadine hydrochloride 665 mcg once daily (QD) | Active | Active | Placebo | Placebo |
| 3 | DYMISTA ® twice daily (BID) | Placebo | Active | Placebo | Active |
| 4 | PATANASE ® twice daily (BID) | Active | Active | Active | Active |
| 5 | Placebo | Placebo | Placebo | Placebo | Placebo |

This study consisted of five visits to the study site and a 12 day at-home dosing period (and 2 days of onsite dosing—a total of 14 days of dosing). Assessment of efficacy endpoints were done out of season, in an EEC facility. After the initial screening visit (Visit 1), patients who met all study criteria (including the main criteria for inclusion: a positive skin prick test (SPT) and a 2 year medical history of allergic rhinitis (AR) to ragweed allergen) underwent further screening/priming in the EEC (Visit 2). During the EEC session patients were exposed to ragweed pollen at a concentration of 3500±500 particles/m$^3$ for 6 hours. Patients used an electronic diary (ePDAT™) to rate their ocular and nasal symptoms every 30 minutes in the EEC Patients who met a minimum qualifying TNSS of 6/12, including a score of at least 2 for nasal congestion on two consecutive diary entries continued in the study. At Visit 3, on the following day (Day 1), patients who met the minimum criteria returned to the EEC for a second consecutive EEC session. Patients were exposed to allergen for approximately 10 hours during this visit. During the first 6 hours, patients used the electronic diary to complete symptom assessments every 30 minutes and met the minimum qualifying symptom score in order to continue. Those who met the minimum qualifying symptom score were randomized to receive one of the five study drugs after the 6 hours time point in the EEC. After dosing (at approximately noon), patients were asked to complete symptom assessments at 5 minute, 10 minutes, 15 minutes, 25 minutes, 30 minute, 45 minutes, 60 minutes and then every 30 minutes for the remainder of the visit Post-treatment symptom assessments in the EEC were used to determine onset of action for study treatments. Patients were then sent home with their study medication to continue at-home BID dosing starting from the evening dose for Day 1. Patients continued at-home dosing for a period of 12 days. Following the 12 days (Days 2-13) of at-home dosing, patients returned to the EEC on Day 14 (Visit 4) for a post-treatment 6-hour priming EEC session. Patients were dosed with the morning dose of study drug one hour prior to entering the EEC. Symptoms were assessed every 30 minutes in the EEC Patients took their last dose of study treatment at midnight on the same day, and returned on the following morning (Day 15. Visit 5) for a 6 hour EEC session Over a period of 6 hours, patients used the electronic diary to complete symptom assessments every 30 minutes. In addition to collection of nasal and ocular symptoms, the electronic diary was used to collect EEC-Quality-of-Life Questionnaires (EEC-QoLQ) at Visits 2, 3, 4 and 5, and acceptability and tolerability at Visit 5. Visit 5 was the final visit for the study.

Priming

Fulfillment of the following criteria on each of two consecutive diary cards reading at priming visit: minimum TNSS of 6 out of 12, including a score of at least 2 for nasal congestion.

Randomization

Patients meeting these same criteria at both priming visits of 3 hours chamber duration in order to proceed to the treatment visit (Visit 3).

At the treatment visit (Visit 3), a minimum TNSS of 6 out of 12 (including a score of at least 2 for nasal congestion).

Drug Formulations

The test product formulations used in the study were as follows:

Test Product 1 (TP-1)

Mometasone Furoate Monohydrate and Olopatadine Hydrochloride Nasal Spray (25 mcg+600 mcg)

Each spray delivered mometasone furoate monohydrate equivalent to 25 mcg mometasone furoate and olopatadine hydrochloride equivalent to 600 mcg olopatadine.

Test Product 2 (TP-2)

Mometasone Furoate Monohydrate and Olopatadine Hydrochloride Nasal Spray (50 mcg+600 mcg)

Each spray delivered mometasone furoate monohydrate equivalent to 50 mcg mometasone furoate and olopatadine hydrochloride equivalent to 600 mcg olopatadine.

Dosage Regimen

1. Investigational Products
    TP-1: Fixed dose combination of Olopatadine hydrochloride (665 mcg) and Mometasone furoate (25 mcg) Nasal Spray: 2 sprays per nostril were delivered Twice daily (BID) for two weeks.
    TP-2: Fixed dose combination of Olopatadine hydrochloride (665 mcg) and Mometasone furoate (50 mcg) Nasal Spray: 2 sprays per nostril were delivered once daily (QD) for two weeks
2. Reference Therapies
    Olopatadine hydrochloride Nasal Spray (PATANASE® 0.6%): 2 sprays per nostril were delivered twice daily for two weeks.
    DYMISTA® (azelastine hydrochloride+fluticasone propionate) 137 mcg/50 mcg Nasal Spray: 1 spray per nostril was delivered twice daily for two weeks.
    Placebo Nasal Spray (based on vehicle of Investigational product): 2 sprays per nostril were delivered twice daily for two weeks.

Key Evaluation Criteria (Clinical Endpoints)

Change from baseline in mean post-treatment Total Nasal Symptoms Score (TNSS) over placebo for fixed dose combination of mometasone furoate and olopatadine hydrochloride. Mean TNSS were calculated over 6 hours in the EEC for post-treatment at Visit 5 (over hours 18 to 24 after the first dosing on Day 14) and matched baseline TNSS in the EEC at Visit 3 (over 6 hours prior to first dosing).

Change from baseline in mean post-treatment TNSS for two regimens of fixed dose combination of mometasone furoate and olopatadine hydrochloride with reference products: DYMISTA® nasal spray and PATANASE® nasal spray. Mean TNSS were calculated over 6 hours in the EEC for post-treatment at Visit 5 (over hours 18 to 24 after the first dosing on Day 14) and matched baseline TNSS in the EEC at Visit 3 (over 6 hours prior to first dosing).

Change from baseline in mean post-treatment TNSS for two regimens of fixed dose combination of mometasone furoate and olopatadine hydrochloride, DYMISTA® nasal spray and PATANASE® nasal spray. Mean post-treatment TNSS were calculated over 6 hours in the EEC for post-treatment at Visit 4 (over hours 1 to 7 after first dosing on Day 14) and matched baseline TNSS in the EEC at Visit 2 (over 6 hours).

Change from baseline in mean post-treatment TNSS for two regimens of fixed dose combination of mometasone furoate and olopatadine hydrochloride compared with reference products: DYMISTA® nasal spray and PATANASE® nasal spray. Mean TNSS were calculated over 12 hours in the EEC for post-treatment (at Visit 4 over 1 to 7 hours after first dosing on Day 14, and at Visit 5 over 18 to 24 hours after first dosing on Day 14) and matched baseline TNSS in the EEC at Visit 2 and Visit 3 (over 12 hours prior to first dosing).

Onset of Action for each treatment of fixed dose combination of mometasone furoate and olopatadine hydrochloride, DYMISTA® and PATANASE® were assessed by comparing change from baseline in post-treatment TNSS between each active treatment and placebo at every time point after the first treatment. Change from baseline in TNSS were calculated at every time point after the first dose of study treatment in the EEC at Visit 3 (i.e., over the last four hours in the EEC at Visit 3) with baseline (Visit 3) defined as the average of the last two time points pre-dosing.

Change from baseline in mean post-treatment Total Symptoms Score (TSS), Individual Nasal Symptoms Scores (NSS, four nasal symptoms of rhinorrhea, pruritus, sneezing and nasal congestion) and TOSS over 6 hours in the EEC at Visit 5 and matched baseline at Visit 3 (over 6 hours prior to first dosing).

Change from baseline in mean post-treatment Total Symptoms Score (TSS), Individual Nasal Symptoms Scores (NSS, four nasal symptoms of rhinorrhea, pruritus, sneezing and nasal congestion) and TOSS over the 6 hours in the EEC at Visit 4 and matched baseline at Visit 2 (over the 6 hours in the EEC).

Change from baseline in mean post-treatment Total Symptoms Score (TSS), Individual Nasal Symptoms Scores (NSS, four nasal symptoms of rhinorrhea, pruritus, sneezing and nasal congestion) and TOSS over 12 hours in the EEC at Visit 4 and Visit 5 and matched baseline over 12 hours in the EEC prior to dosing at Visit 2 and Visit 3.

EEC-QoLQ for all treatment arms by comparing 1) pre-EEC-QoLQ at baseline (Visit 2) with pre-EEC at Visit 4; 2) post-EEC at baseline Visit 2 with post-EEC at Visit 4; 3) after 6 hours in the EEC at Visit 3 (prior to first dosing) with post-EEC at Visit 5.

Reflective tolerability and acceptability for treatment arms compared to placebo post-EEC at Visit 5.

Results

Table B shows a summary of the TNSS change from baseline to post-treatment over 6 hours in EEC (ITT Population).

TABLE B

| Parameters | | Placebo | TP-1 | TP-2 | DYMISTA ® ® (Reference) | PATANASE (Reference) |
|---|---|---|---|---|---|---|
| | N | 36 | 36 | 36 | 36 | 36 |
| Baseline EEC | Mean | 7.64 | 8.07 | 8.20 | 8.67 | 8.27 |
| EEC at the end of treatment (2 weeks) | Mean | 6.61 | 3.31 | 3.94 | 4.80 | 6.38 |
| % Change from Baseline | | 13.35 | 58.98 | 51.95 | 45.67 | 22.85 |

Table C shows a summary of the TNSS change from baseline to post-treatment over 12 hours in EEC (ITT Population). (The data for NASONEX in Table C is sourced from its U.S. FDA approved label.)

TABLE C

| Parameters | | TP-1 | TP-2 | PATANASE ® (Reference) | NASONEX ®* | DYMISTA ® (Reference) |
|---|---|---|---|---|---|---|
| | N | 36 | 36 | 36 | 176 | 36 |
| Baseline EEC | Mean | 7.58 | 7.85 | 7.90 | 9.60 | 8.25 |
| EEC at the end of treatment (2 weeks) | Mean | 2.85 | 3.36 | 5.72 | — | 4.34 |
| % Change from Baseline | | 62.4 | 57.07 | 27.5 | 27.92 | 48.24 |

*NASONEX ® (mometasone furoate nasal spray) US FDA Approved label (Jan. 19, 2011)

Table D shows a summary of the TOSS change from baseline to post-treatment over 12 hours in EEC (ITT Population).

TABLE D

| Parameters | | TP-1 | TP-2 | PATANASE ® (Reference) | DYMISTA ® (Reference) |
|---|---|---|---|---|---|
| | N | 36 | 36 | 36 | 36 |
| Baseline EEC | Mean | 3.97 | 4.17 | 3.92 | 4.54 |
| EEC at the end of treatment (2 weeks) | Mean | 1.97 | 2.34 | 2.82 | 2.82 |
| % Change from Baseline | | 50.37 | 43.6 | 28.3 | 37.88 |

The results of the study show that a combination of mometasone furoate and olopatadine hydrochloride, when administered nasally to a human patient, provides an effective treatment of seasonal allergic rhinitis and clinically significant reduction in both nasal and non-nasal symptoms associated therewith. The magnitude of this relief for TNSS was clinically relevant (i.e., greater than 2 units in difference—which is generally considered as clinically relevant—between the Test Products and Placebo). Test Product-1 showed overall better symptom relief as compared to the Reference Products (PATANASE® and DYMISTA®). Onset of action occurred by 10 minutes for TP-1 based on iTNSS change from baseline after the first dose at Visit 3 (−1.26). However, onset of action could not be defined for TP-2, DYMISTA, and PATANASE as statistically significant differences in iTNSS change from baseline between these treatments and placebo treatment were not observed at any 2 consecutive time points.

Example 6

Phase II Clinical Study of Fixed Dose Combination of Mometasone and Olopatadine Nasal Spray in Human Patients The study is a double-blind, randomized, parallel-group, comparative study to evaluate the efficacy, safety and tolerability of two different strengths and regimens of a fixed dose combination of mometasone furoate and olopatadine hydrochloride nasal spray compared with a placebo nasal spray and individual monotherapy formulations of olopatadine hydrochloride nasal spray and mometasone furoate nasal spray, in subjects (12 years of age and older) with seasonal allergic rhinitis (SAR).

Key Objectives
- To compare the efficacy of mometasone furoate and olopatadine hydrochloride nasal spray once daily and mometasone furoate and olopatadine hydrochloride nasal spray twice daily with the placebo nasal spray and with the individual constituent monotherapies at the same dose in the same vehicle over 14 days of study treatment.
- To compare the onset of action between mometasone furoate and olopatadine hydrochloride nasal spray once daily and mometasone furoate and olopatadine hydrochloride nasal spray twice daily with the placebo and the individual constituent monotherapies at the same dose in the same vehicle, after the first dose of study drug administration.
- To assess the safety and tolerability of individual treatment arms.

TABLE E

Investigational products and their administration

| Code | Investigational product(s) | Administration |
| --- | --- | --- |
| TP-1 | Olopatadine hydrochloride + mometasone furoate (665 μg + 25 μg) nasal sprays | Twice daily (BID) in morning and evening |
| TP-2 | Olopatadine hydrochloride + mometasone furoate (665 μg + 50 μg) nasal spray | Once daily (QD) in morning |
| GO-1 | Olopatadine hydrochloride (665 μg) nasal spray | Once daily (QD) in morning |
| GO-2 | Olopatadine hydrochloride (665 μg) nasal spray | Twice daily (BID) in morning and evening |
| GM-1 | Mometasone furoate (50 μg) nasal spray | Once daily (QD) in morning |
| GM-2 | Mometasone furoate (25 μg) nasal spray | Twice daily (BID) in morning and evening |

Sample Size:
A total of 1,106 randomized subjects (158 subjects per treatment arm) were enrolled in the study.

Key Subject Selection Criteria:
- Age ≥12 and older inclusive of either sex.
- Documented clinical history of SAR (for at least 2 years preceding the screening visit) with exacerbations (clinical evidence of active symptoms) and exhibiting a documented positive SPT (wheal diameter at least 5 mm greater than control wheal) to mountain cedar allergen.
- A 12-hour reflective TNSS≥8 out of a possible 12 and a congestion score of ≥2 for the AM assessment at the Screening Visit (Visit 1).

Study Design:
Subjects were randomized to treatment in a 1:1:1:1:1:1:1 ratio to the following seven treatment arms, at multiple study sites.

The double-dummy design including two identical nasal spray bottles (one for morning [AM] dosing and one for evening [PM] dosing) are utilized for this study (Table F). The double-dummy design is ensured for adequate blinding considering that treatments being compared vary in dosing frequency (BID compared with QD).

TABLE F

Treatment Administration Using Two Identical Bottles of Nasal Sprays (2 sprays per nostril, total 4 sprays each bottle, per day)

| Code | Treatment/Arm | Morning (AM) $1^{st}$ bottle | Evening (PM) $2^{nd}$ bottle |
| --- | --- | --- | --- |
| TP-1 | Olopatadine hydrochloride 665 μg + mometasone furoate 25 μg twice daily (BID) | Active | Active |
| TP-2 | Olopatadine hydrochloride 665 μg + mometasone furoate 50 μg once daily (QD) | Active | Placebo |
| GO-1 | Olopatadine hydrochloride nasal spray (665 μg) once daily (QD) | Active | Placebo |
| GO-2 | Olopatadine hydrochloride nasal spray (665 μg) twice daily (BID) | Active | Active |
| GM-1 | Mometasone furoate nasal spray (50 μg) once daily (QD) | Active | Placebo |
| GM-2 | Mometasone furoate nasal spray (25 μg) twice daily (BID) | Active | Active |
| Pbo | Placebo nasal spray | Placebo | Placebo |

This study consisted of four visits to the study site. After the initial screening visit (Visit 1), subjects who met all study selection criteria were required to undergo a single-blind placebo run-in period for 7-10 days. Following the completion of the run-in period, eligible subjects meeting the randomization criteria were enrolled and randomized to one of the seven treatment arms. Subjects were dispensed medication as per the randomization list. Randomized subjects were required to undergo a 2 week (14 days) treatment period as per the protocol to assess the efficacy and safety of the assigned treatment.

Key Evaluation Criteria (Clinical Endpoints):

Primary Endpoint
- Change from baseline in average AM and PM subject-reported 12-hour rTNSS (reflective TNSS) over the 14-day treatment period.

Secondary Endpoints
- Change from baseline in average AM and PM subject-reported 12-hour iTNSS (instantaneous TNSS) over the 14 day treatment period.
- Change from baseline in average AM and PM subject-reported 12-hour rTOSS (reflective TOSS) over the 14-day treatment period.
- Onset of action for each treatment are assessed by comparing the change from baseline in post-treatment iTNSS between each active treatment and placebo at defined time points (prior to first dose (pre-dose), 15 min, 30 min, 45 min. 60 min, 90 min, 120 min, 150 min, 180 min, 210 min, and 240 min) after the first study treatment for 4 hours.
- Change from baseline in the rhinoconjunctivitis quality of life questionnaire (RQLQ) on day 15 between treatment arms for subjects with impaired quality of life at baseline as defined by the RQLQ Score at the randomization visit (RV) of 3.0 or greater (RQLQ population).

Tertiary Efficacy Endpoints
Nasal Symptoms:
  Change from baseline in AM subject-reported rTNSS over the 14-day treatment period.
  Change from baseline in AM subject-reported iTNSS over the 14-day treatment period.
  Change from baseline in PM subject-reported rTNSS over the 14-day treatment period.
  Change from baseline in PM subject-reported iTNSS over the 14-day treatment period.
  Change from baseline in subject-reported reflective individual nasal symptoms over the 14-day treatment period (AM, PM and average of AM and PM).
  Change from baseline in subject-reported instantaneous individual nasal symptoms over the 14-day treatment period (AM, PM and average of AM and PM).
  Change from baseline in average AM and PM subject-reported rTNSS and iTNSS for each day.
  Change from baseline in AM subject-reported rTNSS and iTNSS for each day.
  Change from baseline in PM subject-reported rTNSS and iTNSS for each day.
Ocular Symptoms:
  Change from baseline in average AM and PM subject-reported iTOSS (instantaneous TOSS) over the 14-day treatment period.
  Change from baseline in AM subject-reported rTOSS over the 14-day treatment period.
  Change from baseline in AM subject-reported iTOSS over the 14-day treatment period.
  Change from baseline in PM subject-reported rTOSS over the 14-day treatment period.
  Change from baseline in PM subject-reported iTOSS over the 14-day treatment period.
  Change from baseline in subject-reported reflective individual ocular symptoms over the 14-day treatment period (AM, PM and average AM and PM).
  Change from baseline in subject-reported instantaneous individual ocular symptoms over the 14-day treatment period (AM. PM and average AM and PM).
  Change from baseline in average of the AM and PM subject-reported rTOSS and iTOSS for each day.
  Change from baseline in AM subject-reported rTOSS and iTOSS for each day.
  Change from baseline in PM subject-reported rTOSS and iTOSS for each day.

The non-nasal symptoms are assessed in a similar manner to the ocular symptoms above.

Physician Assessed Nasal Symptom Score (PNSS) and Rhinoconjuntivitis Quality of Life Questionnaire (RQLQ):
  Physician assessed Nasal Symptom Score (PNSS) and physician assessed individual nasal symptoms at Day 15 (Visit 4).
  Individual domains of the RQLQ at Day 15 (Visit 4) for the RQLQ population (defined as subject with impaired Quality of Life at baseline).
  RQLQ at Day 15 (Visit 4) for the full analysis set (FAS).

Results

Table G shows a summary of the primary clinical endpoint (rTNSS) and secondary clinical endpoints (iTNSS, rTOSS, onset of action and RQLQ) observed during this Phase II study. For comparison of the combination therapy against a monotherapy, a p-value below 0.05 is considered statistically significant.

TABLE G

| Treatment Arm | Primary Clinical Endpoint rTNSS | Secondary Clinical endpoints | | | |
| --- | --- | --- | --- | --- | --- |
| | | iTNSS | rTOSS | Onset of Action | RQLQ |
| TP-2 vs Pbo | −1.10* $p < 0.001$* | −1.10 $p < 0.001$* | −0.55 $p = 0.004$* | 150 min. Statistically significant at all time points after 150 min (except 180 min)* | −0.48 $p = 0.004$* |
| TP-2 vs GO-1 | −0.77 $p = 0.002$* | −0.86 $p = 0.0003$* | −0.36 $p = 0.65$ | NA | −0.29 $p = 0.085$ |
| TP-2 vs GM-1 | −0.35 $p = 0.15$ | −0.34 $p = 0.145$ | −0.37 $p = 057$ | NA | −0.13 $p = 0.429$ |
| TP-1 vs Pbo | −1.17* $p < 0.001$* | −1.10 $p < 0.001$* | −0.41 $p = 0.032$ | Not statistically significant at all time points | −0.56 $p = 0.0009$* |
| TP-1 vs GO-2 | −0.49 $p = 0.048$* | −0.45 $p = 0.058$ | −0.03 $p = 0.849$ | NA | −0.25 $p = 0.135$ |
| TP-1 vs GM-2 | −0.71 $p = 0.004$* | −0.65 $p = 0.006$* | −0.40 $p = 040$* | NA | −0.41 $P = 0.014$* |

*indicates statistical significance

As can be seen from Table G, the combination of mometasone fuorate and olopatadine hydrochloride, when administered once daily (TP-2) or twice daily (TP-1) is statistically superior to placebo (p<0.000 for the primary endpoint, change in rTNSS from baseline. The combination of mometasone fuorate and olopatadine hydrochloride, when administered once daily (TP-2) or twice daily (TP-1) also met secondary clinical endpoints in the trial, supportive of its efficacy in the treatment of seasonal allergic rhinitis (SAR). The combination of mometasone fuorate and olopatadine hydrochloride, when administered twice daily (TP-1) was also statistically superior to the individual monotherapies (GO-2 and GM-2) for both primary (rTNSS) and secondary endpoints (iTNSS).

Table G2 shows the least squares mean difference in individual reflective nasal symptoms scores for TP-1 and TP-2 versus placebo.

TABLE G2

Least Squares Mean Difference in Individual Reflective Nasal Symptom Scores with TP-1 or TP-2 versus Placebo

| | Least squares mean difference (97.5% confidence interval) | P value |
|---|---|---|
| TP-1 | | |
| Rhinorrhea | −0.27 (−0.42, −0.12) | <0.001 |
| Nasal congestion | −0.24 (−0.38, −0.99) | <0.001 |
| Nasal itching | −0.27 (−0.43, −0.11) | <0.001 |
| Sneezing | −0.39 (−0.57, −0.22) | <0.001 |
| TP-2 | | |
| Rhinorrhea | −0.26 (−0.40, −0.11) | <0.001 |
| Nasal congestion | −0.22 (−0.37, −0.08) | <0.001 |
| Nasal itching | −0.26 (−0.42, −0.10) | <0.001 |
| Sneezing | −0.37 (−0.55, −0.20) | <0.001 |

Table H shows a summary of the treatment emergent adverse events (TEAEs) observed during this Phase II study.

TABLE H

| | Pbo (N = 159) | TP-2 (N = 158) | GM-1 (N = 160) | GO-1 (N = 158) | TP-1 (N = 157) | GM-2 (N = 159) | GO-2 (N = 160) |
|---|---|---|---|---|---|---|---|
| At least 1 TEAE | 13 (8.2%) | 15 (9.5%) | 15 (9.4%) | 17 (10.8%) | 17 (10.8%) | 10 (6.3%) | 25 (15.6%) |
| Dysgeusia | 0 | 2 (1.3%) | 0 | 2 (1.3%) | 2 (1.3%) | 0 | 5 (3.1%) |
| Headache | 1 (0.6%) | 6 (3.8%) | 2 (1.3%) | 1 (0.6%) | 0 | 1 (0.6%) | 1 (0.6%) |

All TEAEs were mild to moderate. Dysgeusia (1.3%) and headache (1.9%) were adverse events (AEs) reported for the combination of mometasone fuorate and olopatadine hydrochloride administered twice daily (BID) and once daily (QD), respectively.

Example 7

Phase III Clinical Study of Fixed Dose Combination of Mometasone and Olopatadine Nasal Spray in Human Patients with SAR, Spring Season This study was a double-blind, randomized, parallel-group, comparative study to evaluate the efficacy, safety and tolerability of a fixed dose combination of mometasone furoate and olopatadine hydrochloride nasal spray compared with a placebo nasal spray and individual monotherapy formulations of olopatadine hydrochloride nasal spray and mometasone furoate nasal spray, in subjects (12 years of age and older) with seasonal allergic rhinitis (SAR), spring season.

Study Objectives
  To compare the efficacy of mometasone furoate and olopatadine hydrochloride nasal spray twice daily with the placebo nasal spray and with the individual constituent monotherapies at the same dose in the same vehicle over 14 days of study treatment.
  To assess the safety and tolerability of individual treatment arms.
  To investigate the pharmacokinetics (PK) of mometasone furoate and olopatadine hydrochloride nasal spray twice daily treatment.

TABLE I

Investigational products and their administration

| Code | Investigational product(s) | Administration |
|---|---|---|
| TP-1 | Olopatadine hydrochloride + mometasone furoate (665 μg + 25 μg) nasal spray | Twice daily (BID) in morning and evening |
| GO-2 | Olopatadine hydrochloride (665 μg) nasal spray | Twice daily (BID) in morning and evening |
| GM-2 | Mometasone furoate (25 μg) nasal spray | Twice daily (BID) in morning and evening |

Sample Size:
  A total of 1,180 randomized subjects (295 subjects per treatment arm) were enrolled in the study.

Key Subject Selection Criteria:
  Age ≥12 and older inclusive of either sex.
  Documented clinical history of SAR (for at least 2 years preceding the screening visit) with exacerbations (clinical evidence of active symptoms) during the study season for mountain season pollen and exhibiting a documented positive SPT (wheal diameter at least 5 mm greater than control wheal) to mountain cedar allergen.
  A 12-hour reflective TNSS≥8 out of a possible 12 and a congestion score of ≥2 for the AM assessment at the Screening Visit (Visit 1).

Study Design:
  Subjects were randomized to treatment in a 1:1:1:1 ratio to the following four treatment arms, at multiple study sites.

TABLE J

Treatment Administration Using Two Identical Bottles of Nasal Sprays (2 sprays per nostril, total 4 sprays each bottle, per day)

| Code | Treatment Arm | Morning (AM) 1st bottle | Evening (PM) 2nd bottle |
|---|---|---|---|
| TP-1 | Olopatadine hydrochloride 665 μg + mometasone furoate 25 μg twice daily (BID) | Active | Active |
| GO-2 | Olopatadine hydrochloride nasal spray (665 μg) twice daily (BID) | Active | Active |
| GM-2 | Mometasone furoate, nasal spray (25 μg) twice daily (BID) | Active | Active |
| Pbo | Placebo nasal spray | Placebo | Placebo |

This study consisted of four visits to the study site. After the initial screening visit (Visit 1), subjects who met all study selection criteria were required to undergo a single-blind placebo run-in period for 7-10 days. Following the completion of the run-in period, eligible subjects meeting the randomization criteria were enrolled and randomized to one of the four treatment arms. Subjects were dispensed medication as per the randomization list. Randomized subjects were required to undergo a 2 week (14 days) treatment period as per the protocol to assess the efficacy and safety of the assigned treatment. Subjects were instructed to record the symptom scores in a symptom assessment diary. They were also scheduled to have at least two blood samples for PK assessment during the treatment period.

Key Evaluation Criteria (Clinical Endpoints):

Primary Endpoint
  Change from baseline in average AM and PM subject-reported 12-hour rTNSS (reflective TNSS) over the 14-day treatment period.

Secondary Endpoints
  Change from baseline in average AM and PM subject-reported 12-hour iTNSS (instantaneous TNSS) over the 14 day treatment period.
  Change from baseline in average AM and PM subject-reported 12-hour rTOSS (reflective TOSS) over the 14-day treatment period.
  Onset of action for each treatment are assessed by comparing the change from baseline in post-treatment iTNSS between each active treatment and placebo at defined time points (prior to first dose (pre-dose), 15 min, 30 min, 45 min, 60 min, 90 min, 120 min, 150 min, 180 min, 210 min, and 240 min) after the first study treatment for 4 hours.
  Change from baseline in the overall Rhinoconjunctivitis Quality of Life questionnaire (RQLQ)-Standardized Activities (RQLQ(S)) score on Day 15 (Visit 4) for the Full Analysis Set (FAS).

Pharmacokinetic Endpoints
  Plasma PK: Maximum plasma concentration ($C_{max}$), time to attain $C_{max}$ ($T_{max}$), and area under the plasma concentration-time curve over the dosing interval ($AUC_{tau}$) will be estimated for mometasone furoate and olopatadine on Day 1 and Day 8 based on the pharmacokinetic analysis set (PKAS).

Tertiary Efficacy Endpoints

Nasal Symptoms:
  Change from baseline in AM subject-reported rTNSS over the 14-day treatment period.
  Change from baseline in AM subject-reported iTNSS over the 14-day treatment period.
  Change from baseline in PM subject-reported rTNSS over the 14-day treatment period.
  Change from baseline in PM subject-reported iTNSS over the 14-day treatment period.
  Change from baseline in subject-reported reflective individual nasal symptoms over the 14-day treatment period (AM, PM and average of AM and PM).
  Change from baseline in subject-reported instantaneous individual nasal symptoms over the 14-day treatment period (AM, PM and average of AM and PM).
  Change from baseline in average AM and PM subject-reported rTNSS and iTNSS for each day.
  Change from baseline in AM subject-reported rTNSS and iTNSS for each day.
  Change from baseline in PM subject-reported rTNSS and iTNSS for each day.

Ocular Symptoms:
  Change from baseline in average AM and PM subject-reported iTOSS (instantaneous TOSS) over the 14-day treatment period.
  Change from baseline in AM subject-reported rTOSS over the 14-day treatment period.
  Change from baseline in AM subject-reported iTOSS over the 14-day treatment period.
  Change from baseline in PM subject-reported rTOSS over the 14-day treatment period.
  Change from baseline in PM subject-reported iTOSS over the 14-day treatment period.
  Change from baseline in subject-reported reflective individual ocular symptoms over the 14-day treatment period (AM, PM and average AM and PM).
  Change from baseline in subject-reported instantaneous individual ocular symptoms over the 14-day treatment period (AM. PM and average AM and PM).
  Change from baseline in average of the AM and PM subject-reported rTOSS and iTOSS for each day.
  Change from baseline in AM subject-reported rTOSS and iTOSS for each day.
  Change from baseline in PM subject-reported rTOSS and iTOSS for each day.

The non-nasal symptoms are assessed in a similar manner to the ocular symptoms above.

Physician assessed Nasal Symptom Score (PNSS), Rhinoconjuntivitis Quality of Life Questionnaire Standardized Activities (RQLQ(S)), and Rhinitis Control Assessment Test (RCAT):
  Change from baseline in PNSS and physician assessed individual nasal symptoms at Day 15 (Visit 4).
  Change from baseline in individual domains of the RQLQ (S) at Day 15 (Visit 4) for the FAS.
  Change from baseline in overall RQLQ(S) score and individual domains of the RQLQ(S) at Day 15 (Visit 4) for the RQLQ(S) analysis set.
  Change from baseline in the RCAT at Day 15 (Visit 4).
  Change from baseline in individual domains of the RCAT at Day 15 (Visit 4).
  Individual domains of the RQLQ at Day 15 (Visit 4) for the RQLQ population (defined as subject with impaired Quality of Life at baseline).
  RQLQ at Day 15 (Visit 4) for the full analysis set (FAS).

Results

Table K shows a summary of the primary clinical endpoint (rTNSS) and secondary clinical endpoints (iTNSS, rTOSS, onset of action and RQLQ) observed during this Phase III study. For comparison of the combination therapy against a monotherapy, a p-value below 0.05 is considered statistically significant.

TABLE K

| Treatment Arm | Primary Clinical Endpoint rTNSS | Secondary Clinical endpoints | | | |
|---|---|---|---|---|---|
| | | iTNSS | rTOSS | Onset of Action | RQLQ |
| TP-1 vs Pbo | −0.98 p < 0.0001* | −0.93 p < 0.0001* | −0.49 p = 0.0014* | 15 min Statistically significant at all time points | −0.43 p = 0.0001 |

TABLE K-continued

| Treatment Arm | Primary Clinical Endpoint rTNSS | Secondary Clinical endpoints | | | |
|---|---|---|---|---|---|
| | | iTNSS | rTOSS | Onset of Action | RQLQ |
| TP-1 vs GO-2 | −0.61 p = 0.0029* | −0.50 p = 0.0050* | −0.09 p = 0.5423 | NA | −0.28 p = 0.0105 |
| TP-1 vs GM-2 | −0.39 p = 0.058 | −0.36 p = 0.0413* | −0.19 p = 0.2113 | NA | −0.20 p = 0.0692 |
| GO-2 vs Pbo | −0.37 p = 0.075 | −0.42 p = 0.0177* | −0.40 p = 0.0100 | statistically significant at 45 mins only | −0.15 p = 0.1659 |
| GM-2 vs Pbo | −0.59 p = 0.004 | −0.57 p = 0.0017* | −0.30 p = 0.0510 | Not statistically significant at all time points | −0.23 p = 0.0345 |

*indicates statistical significance.

As can be seen from Table K, the combination of mometasone fuorate and olopatadine hydrochloride, when administered twice daily (TP-1) is statistically superior to placebo (p<0.0001) for the primary endpoint, change in TNSS from baseline, and is statistically superior to olopatadine hydrochloride monotherapy (GO-2). The secondary endpoints were also statistically significant for combination of mometasone fuorate and olopatadine hydrochloride, when administered twice daily (TP-1), supportive of its efficacy in the treatment of seasonal allergic rhinitis (SAR).

The combination of mometasone fuorate and olopatadine hydrochloride, when administered twice daily (TP-1) also exhibited a faster (rapid) onset of action (an onset of action within 15 minutes), as measured by iTNSS, when compared to olopatadine hydrochloride monotherapy or mometasone fuorate monotherapy.

All TEAEs were mild to moderate. Dysgeusia (3.3%) and headache (0.7%) reported as adverse events for the combination of mometasone fuorate and olopatadine hydrochloride administered twice daily (BID).

The pharmacokinetics (PK) of TP-1 were measured for a subset of patients in the phase II clinical study on day 1 and day 8 (steady state). The PK results for patients receiving TP-1 are provided below.

Example 8

Phase III Clinical Study of Fixed Dose Combination of Mometasone and Olopatadine Nasal Spray in Human Patients with SAR, Fall and Mountain Cedar Season This study was a double-blind, randomized, parallel-group, comparative study to evaluate the efficacy, safety and tolerability of a fixed dose combination of mometasone furoate and olopatadine hydrochloride nasal spray compared with a placebo nasal spray and individual monotherapy formulations of olopatadine hydrochloride nasal spray and mometasone furoate nasal spray, in subjects (12 years of age and older) with seasonal allergic rhinitis (SAR), fall and mountain cedar season.

Study Objectives
- To compare the efficacy of mometasone furoate and olopatadine hydrochloride nasal spray twice daily with the placebo nasal spray and with the individual constituent monotherapies at the same dose in the same vehicle over 14 days of study treatment.
- To assess the safety and tolerability of individual treatment arms.

| | Olopatadine | | | Mometasone furoate | |
|---|---|---|---|---|---|
| PK parameter | Day 1 | Day 8 | PK parameter | Day 1 | Day 8 |
| $C_{max}$ (ng/mL) | n = 26 | n = 25 | $C_{max}$ (pg/mL) | n = 26 | n = 26 |
| Mean (SD) | 19.82 (6.36) | 19.80 (7.01) | Mean (SD) | 6.78 (2.71) | 9.92 (3.74) |
| CV % | 32.12 | 35.39 | CV % | 39.96 | 37.69 |
| Min-Max | 8.70-31.60 | 9.67-37.30 | Min-Max | 2.67-12.80 | 3.58-16.10 |
| Geo Mean (Geo CV %) | 18.77 (35.61) | 18.70 (35.34) | Geo Mean (Geo CV %) | 6.27 (42.80) | 9.17 (43.88) |
| $AUC_{tau}$ (ng*hr/mL) | n = 26 | n = 24 | $AUC_{tau}$ (pg*hr/mL) | n = 26 | n = 25 |
| Mean (SD) | 75.48 (20.02) | 88.77 (23.87) | Mean (SD) | 28.56 (13.33) | 58.40 (27.00) |
| CV % | 26.53 | 26.89 | CV % | 46.67 | 46.23 |
| Min-Max | 39.33-116.80 | 53.35-138.34 | Min-Max | 12.11-72.54 | 25.68-124.05 |
| Geo Mean (Geo CV %) | 72.90 (27.67) | 85.74 (27.54) | Geo Mean (Geo CV %) | 26.16 (43.51) | 52.67 (49.48) |
| $T_{max}$ (hour) | n = 26 | n = 26 | $T_{max}$ (hour) | n = 26 | n = 26 |
| Median (range) | 1.00 (0.25-3) | 1.00 (0.25-2) | Median (range) | 1.00 (0.25-2) | 1.00 (0.25-2) |

TABLE L

Investigational products and their administration

| Code | Investigational product(s) | Administration |
|---|---|---|
| TP-1 | Olopatadine hydrochloride + mometasone furoate (665 µg + 25 µg) nasal spray | Twice daily (BID) in morning and evening |
| GO-2 | Olopatadine hydrochloride (665 µg) nasal spray | Twice daily (BID) in morning and evening |
| GM-2 | Mometasone furoate (25 µg) nasal spray | Twice daily (BID) in morning and evening |

Sample Size:

A total of 1,176 randomized subjects (~294 subjects per treatment arm) were enrolled in the study. For this study, the subject population is adult and adolescent subjects (12 years of age and older) with SAR who exhibit symptoms of SAR during the fall allergy season to the relevant seasonal allergen (e.g., ragweed).

Study Design:

Subjects were randomized to treatment in a 1:1:1:1 ratio to the following four treatment arms, at multiple study sites.

TABLE M

Treatment Administration Using Two Identical Bottles of Nasal Sprays (2 sprays per nostril, total 4 sprays each bottle, per day)

| Code | Treatment Arm | Morning (AM) 1$^{st}$ bottle | Evening (PM) 2$^{nd}$ bottle |
|---|---|---|---|
| TP-1 | Olopatadine hydrochloride 665 µg + mometasone furoate 25 µg twice daily (BID) | Active | Active |
| GO-2 | Olopatadine hydrochloride nasal spray (665 µg) twice daily (BID) | Active | Active |
| GM-2 | Mometasone furoate, nasal spray (25 µg) twice daily (BID) | Active | Active |
| Pbo | Placebo nasal spray | Placebo | Placebo |

This study consisted of four visits to the study site. After the initial screening visit (Visit 1), subjects who met all study selection criteria were required to undergo a single-blind placebo run-in period for 7-10 days. Following the completion of the run-in period, eligible subjects meeting the randomization criteria were enrolled and randomized to one of the four treatment arms. Subjects were dispensed medication as per the randomization list. Randomized subjects were required to undergo a 2 week (14 days) treatment period as per the protocol to assess the efficacy and safety of the assigned treatment. Subjects were instructed to record the symptom scores in a symptom assessment diary.

Key Evaluation Criteria (Clinical Endpoints):

Primary Endpoint

Change from baseline in average AM and PM subject-reported 12-hour rTNSS (reflective TNSS) over the 14-day treatment period.

Secondary Endpoints

Change from baseline in average AM and PM subject-reported 12-hour iTNSS (instantaneous TNSS) over the 14 day treatment period.

Change from baseline in average AM and PM subject-reported 12-hour rTOSS (reflective TOSS) over the 14-day treatment period.

Onset of action for each treatment are assessed by comparing the change from baseline in post-treatment iTNSS between each active treatment and placebo at defined time points (prior to first dose (pre-dose), 15 min, 30 min, 45 min, 60 min, 90 min. 120 min. 150 min. 180 min, 210 min. and 240 min) after the first study treatment for 4 hours.

Change from baseline in the overall Rhinoconjunctivitis Quality of Life questionnaire (RQLQ)-Standardized Activities (RQLQ(S)) score on Day 15 (Visit 4) for the Full Analysis Set (FAS).

Tertiary Efficacy Endpoints

Nasal Symptoms:

Change from baseline in AM subject-reported rTNSS over the 14-day treatment period.

Change from baseline in AM subject-reported iTNSS over the 14-day treatment period.

Change from baseline in PM subject-reported rTNSS over the 14-day treatment period.

Change from baseline in PM subject-reported iTNSS over the 14-day treatment period.

Change from baseline in subject-reported reflective individual nasal symptoms over the 14-day treatment period (AM, PM and average of AM and PM).

Change from baseline in subject-reported instantaneous individual nasal symptoms over the 14-day treatment period (AM, PM and average of AM and PM).

Change from baseline in average AM and PM subject-reported rTNSS and iTNSS for each day.

Change from baseline in AM subject-reported rTNSS and iTNSS for each day.

Change from baseline in PM subject-reported rTNSS and iTNSS for each day.

Ocular Symptoms:

Change from baseline in average AM and PM subject-reported iTOSS (instantaneous TOSS) over the 14-day treatment period.

Change from baseline in AM subject-reported rTOSS over the 14-day treatment period.

Change from baseline in AM subject-reported iTOSS over the 14-day treatment period.

Change from baseline in PM subject-reported rTOSS over the 14-day treatment period.

Change from baseline in PM subject-reported iTOSS over the 14-day treatment period.

Change from baseline in subject-reported reflective individual ocular symptoms over the 14-day treatment period (AM, PM and average AM and PM).

Change from baseline in subject-reported instantaneous individual ocular symptoms over the 14-day treatment period (AM. PM and average AM and PM).

Change from baseline in average of the AM and PM subject-reported rTOSS and iTOSS for each day.

Change from baseline in AM subject-reported rTOSS and iTOSS for each day.

Change from baseline in PM subject-reported rTOSS and iTOSS for each day.

The non-nasal symptoms are assessed in a similar manner to the ocular symptoms above.

Physician assessed Nasal Symptom Score (PNSS), Rhinoconjuntivitis Quality of Life Questionnaire Standardized Activities (RQLQ(S)), and Rhinitis Control Assessment Test (RCAT):

Change from baseline in PNSS and physician assessed individual nasal symptoms at Day 15 (Visit 4).

Change from baseline in individual domains of the RQLQ (S) at Day 15 (Visit 4) for the FAS.

Change from baseline in overall RQLQ(S) score and individual domains of the RQLQ(S) at Day 15 (Visit 4) for the RQLQ(S) Analysis Set.

Change from baseline in the RCAT at Day 15 (Visit 4).

Change from baseline in individual domains of the RCAT at Day 15 (Visit 4).

Results

Table N shows a summary of the primary clinical endpoint (rTNSS) and secondary clinical endpoints (iTNSS, rTOSS, onset of action and RQLQ) observed during this Phase III study. For comparison of the combination therapy against a monotherapy, a p-value below 0.05 is considered statistically significant.

TABLE N

| Treatment Arm | Primary Clinical Endpoint rTNSS | Secondary Clinical Endpoints | | | |
|---|---|---|---|---|---|
| | | iTNSS | rTOSS | Onset of Action | RQLQ |
| TP-1 vs. Pbo | −1.09 (p < 0.001)* | −0.94 (p < 0.001)* | −0.52 (p = 0.001)* | 15 minutes. Statistically significant at all time points. | −0.45 (p = 0.0001)* |
| TP-1 vs. GO-2 | −0.44 (p = 0.028)* | −0.41 (p = 0.0035)* | −0.17 (p = 0.297) | N/A | −0.31 (p = 0.0090)* |
| TP-1 vs. GM-2 | −0.47 (p = 0.019)* | −0.51 (p = 0.008)* | −0.35 (p = 0.030)* | N/A | −0.09 (p = 0.423) |
| GO-2 vs. Pbo | −0.64 (p = 0.001)* | −0.54 (p = 0.005)* | −0.35 (p = 0.029)* | 15 minutes. Statistically significant at all time points. | −0.14 (p = 0.221) |
| GM-2 vs. Pbo | −0.62 (p = 0.002)* | −0.44 (p = 0.023)* | −0.17 (p = 0.282) | Not statistically significant at any time point. | −0.36 (p = 0.0024)* |

*indicates statistical significance

As can be seen from Table N, the combination of mometasone fuorate and olopatadine hydrochloride, when administered twice daily (TP-1) is statistically superior to placebo (p<0.0001) for the primary endpoint, change in rTNSS from baseline, and is statistically superior to olopatadine hydrochloride monotherapy (GO-2) and mometasone fuorate monotherapy (GM-2). The secondary endpoints were also statistically significant for combination of mometasone fuorate and olopatadine hydrochloride, when administered twice daily (TP-1), supportive of its efficacy in the treatment of seasonal allergic rhinitis (SAR).

Table N2 shows the leas squares mean difference in individual reflective and instantaneous nasal symptoms scores for the TP-1 group versus the placebo group.

TABLE N2

Least Squares Mean Difference in Individual Reflective and Instantaneous Nasal Symptom Scores with TP-1 versus Placebo

| | Least squares mean difference (97.5% confidence interval) | P value |
|---|---|---|
| Reflective | | |
| Rhinorrhea | −0.30 (−0.41, −0.19) | <0.001 |
| Nasal congestion | −0.20 (−0.30, −0.09) | <0.001 |
| Nasal itching | −0.23 (−0.34, −0.12) | <0.001 |
| Sneezing | −0.41 (−0.53, −0.29) | <0.001 |
| Instantaneous | | |
| Rhinorrhea | −0.29 (−0.39, −0.18) | <0.001 |
| Nasal congestion | −0.19 (−0.29, −0.09) | <0.001 |
| Nasal itching | −0.21 (−0.32, −0.10) | <0.001 |
| Sneezing | −0.29 (−0.41, −0.18) | <0.001 |

The combination of mometasone fuorate and olopatadine hydrochloride, when administered twice daily (TP-1) also exhibited a faster (rapid) onset of action (an onset of action within 15 minutes), as measured by iTNSS, when compared to olopatadine hydrochloride monotherapy or mometasone fuorate monotherapy.

All TEAEs were mild to moderate. Dysgeusia (3.8%) nasal discomfort (1%) and urinary tract infection (1%) were reported adverse events for the combination of mometasone fuorate and olopatadine hydrochloride administered twice daily (BID).

Example 9

Phase III Clinical Study of Fixed Dose Combination of Mometasone and Olopatadine Nasal Spray in Human Patients The study is a double-blind, randomized, parallel-group, comparative study to evaluate the long-term safety, efficacy, and tolerability of a fixed dose combination of mometasone furoate and olopatadine hydrochloride nasal spray compared with two placebo nasal sprays, in subjects (12 years of age and older) with perennial allergic rhinitis (PAR).

Study Objectives

To compare the long-term safety and tolerability of mometasone furoate and olopatadine hydrochloride nasal spray twice daily with two placebo nasal sprays at the same dose in the same vehicle over 52 weeks of study treatment in subjects with PAR.

A secondary objective is to evaluate the long-term efficacy of a fixed dose combination of mometasone furoate and olopatadine hydrochloride nasal spray compared with a placebo nasal spray formulations (pH=3.7) in subjects with PAR.

Key Subject Selection Criteria:

Male and non-pregnant females aged ≥12 years.

A history of PAR for a minimum of 2 years and a positive skin prick test to at least 1 relevant allergen.

An AM subject-reported Reflective Total Nasal Symptom Score (iTNSS)≥5 out of a possible 12 and a congestion score 2 for the morning (AM) assessment at the Screening Visit (Visit 1).

At the end of the placebo run-in period, to be eligible for randomization, the subject had not experienced an AE that would result in not meeting the Screening inclusion criteria.

Minimum AM subject-reported rTNSS of an average of 5 (out of a possible 12) during the last 4 days of the run-in period (last 4 consecutive AM assessments from the Day 3 AM assessment to the AM assessment on the day of randomization)

Had an AM subject-reported reflective nasal congestion score of an average 2 or greater during the last 4 days of the run-in period (last 4 consecutive AM assessments from the Day 3 AM assessment to the AM assessment on the day of randomization)

Study Design:

A total of 601 randomized subjects were enrolled in the study. Subjects were randomized to treatment in a 4:1:1 ratio to 3 treatment groups, at multiple site. The treatment groups are provided in Table O below.

TABLE O

Investigational products and their administration

| Code | Investigational product(s) | Administration |
| --- | --- | --- |
| TP-1 | Olopatadine hydrochloride + mometasone furoate (665 µg + 25 µg) nasal spray | Twice daily (BID) in morning and evening |
| Pbo-1 | Placebo nasal spray, pH 3.7 | Placebo - Twice daily (BID) in morning and evening |
| Pbo-2 | Placebo nasal spray, pH 7.0 | Placebo - Twice daily (BID) in morning and evening |

This study consisted of twelve visits to the study site. After the initial screening visit (Visit 1), subjects who met all study selection criteria underwent a single-blind placebo run-in period for 7-10 days. Following the completion of the run-in period, eligible subjects meeting the randomization criteria were enrolled and randomized to one of the three treatment arms. Randomized subjects underwent a 52 week treatment period as per the protocol to assess the efficacy and safety of the assigned treatment.

Key Evaluation Criteria (Clinical Endpoints):

Primary Endpoints

Proportion of subjects with treatment-emergent adverse events (TEAEs).

Proportion of subjects with treatment-related TEAEs.

Incidence, type, and severity of the TEAEs after 30 weeks of study treatment.

Incidence, type, and severity of the TEAEs after 52 weeks of study treatment.

Clinical laboratory assessments (hematology, serum biochemistry, and urinalysis) at baseline, Week 30, and Week 52.

Vital signs, physical examinations (PE), and focused cars, nose, and throat (ENT) and eye examinations at baseline, Week 30, and Week 52.

Secondary Endpoints

Efficacy Endpoints

Change from baseline in the average AM subject-reported rTNSS over the first 6, 30, and 52 weeks of treatment.

Change from baseline in the average AM subject-reported instantaneous Total Nasal Symptom Score (iTNSS) over the first 6, 30, and 52 weeks of treatment.

Change from baseline in the overall Rhinoconjunctivitis Quality of Life Questionnaire Standardized Activities (RQLQ(S)) score at Weeks 6, 30, and 52 for the Full Analysis Set (FAS).

Other Efficacy Endpoints

Other endpoints included other assessments of AM subject-reported individual nasal symptoms, AM subject-reported rTNSS and iTNSS from baseline to the end of each treatment week. Physician-assessed Nasal Symptom Score and physician-assessed individual nasal symptoms, individual domains of the RQLQ for the FAS population, and change from baseline in the Rhinitis Control Assessment Test and individual domains of Rhinitis Control Assessment Test.

Data Sets Analyzed

The Full Analysis Set (FAS) consisted of all subjects who were randomized and received at least one dose of investigational product and had at least one post-baseline efficacy assessment. This was the primary analysis set for efficacy analyses.

The Per Protocol Set (PPS) consisted of the subset of the FAS who did not meet criteria for PPS exclusion. The PPS was a secondary analysis set for the efficacy analyses (except for RQLQ(S)).

The Safety Analysis Set (SAS) consisted of all subjects who took at least one dose of study medication following randomization, and was used for all safety analyses.

The RQLQ(S) Analysis Set consisted of all English-speaking subjects ≥18 years old with impaired quality of life at baseline as defined by RQLQ(S) Score at the Randomization Visit (Visit 2) of 3.0 or greater Efficacy Analysis Efficacy analysis was conducted on the FAS and PPS.

Change from baseline in average AM rTNSS and iTNSS over the first 6, 30, and 52 weeks of treatment was analyzed using an analysis of covariance (ANCOVA) model adjusting for study treatment group, site, and baseline (defined as the average of the last 4 consecutive AM assessments during the last 4 days of the run-in period from the Day −3 AM assessment to the AM assessment on the day of randomization). Least squares means (LSMs) of the treatment differences and associated 95% confidence intervals (95% CIs) and p-values were presented.

Changes from baseline in rTNSS and iTNSS at the end of each week of treatment and changes from baseline in individual nasal symptom scores over the first 6, 30, and 52 weeks (and at the end of each treatment week) of the treatment period were analyzed in a similar manner as described above.

Changes from baseline in RQLQ(S) at Weeks 6, 30, and 52 were analyzed for the FAS and the RQLQ(S) Analysis Set using ANCOVA models adjusting for study treatment group, site, and baseline RQLQ(S) (linear, continuous covariate). At each time-point, only completers of the respective visit were analyzed.

The analyses of RCAT results were similar to the RQLQ (S) analyses except that it was performed only for the FAS.

Safety Analysis

Adverse events occurring after the first dose of randomized study medication were defined as TEAEs.

The safety endpoints related to AEs were:

Proportion of subjects with TEAEs.

Proportion of subjects with treatment-related TEAEs.

Incidence, type, and severity of the TEAEs after 30 weeks of study treatment.
Incidence, type, and severity of the TEAEs after 52 weeks of study treatment.

Results

Safety Analysis

The table below summarizes the safety analysis for the three treatment groups over the 52 week administration period.

| Safety Analysis | TP-1 | Pbo-1 (pH = 3.7) | Pbo-2 (pH = 7.0) |
|---|---|---|---|
| Subjects with a least one TEAE: n (%) | 203 (52%) | 41 (41%) | 54 (54%) |
| TEAEs resulting in discontinuation: n (%) | 15 (3.8%) | 2 (2.0%) | 3 (3.0%) |
| SAEs (all considered not related) | 7 (1.5%) | 2 (2.0%) | 3 (1.5%) |

As can be seen, there was no meaningful differences between the three treatment groups. The majority of TEAEs were mild to moderate severity and considered "not related" by the investigator. The TP-1 treatment was safe and well tolerated, with safety profiles consistent with those expected for the individual monotherapy components. No deaths were reported during the study.

Efficacy Analysis

The table below summarizes the results for the efficacy endpoint: nasal symptoms average AM Reflective Total Nasal Symptoms (rTNSS, last 12 hours) (full set analysis, FAS).

| | TP-1 vs. Pbo-1 (pH = 3.7) | | |
|---|---|---|---|
| | 6 weeks | 30 weeks | 52 Weeks |
| N (TP-1/Pbo-1) | 319/99 | 391/99 | 391/99 |
| Treatment Difference | −0.81 | −0.96 | −0.91 |
| 95% CI | −1.29, −0.32 | −1.41, −0.50 | −1.35, −0.47 |
| p-Value | 0.0012* | <0.0001* | <0.0001* |

*Statistically Significant

As can be seen, TP-1 demonstrated a statistically significant and meaningful improvement in rTNSS versus Pbo-1 (pH=3.7) over the first 6, 30 and 52 weeks of the study.

The table below summarizes the results for the efficacy endpoint: nasal symptoms average AM Instantaneous Total Nasal Symptoms (iTNSS, last 12 hours) (full set analysis, FAS).

| | TP-1 vs. Pbo-1 (pH = 3.7) | | |
|---|---|---|---|
| | 6 weeks | 30 weeks | 52 Weeks |
| N (TP-1/Pbo-1) | 319/99 | 391/99 | 391/99 |
| Treatment Difference | −0.66 | −0.83 | −0.75 |
| 95% CI | −1.12, −0.20 | −1.26, −0.39 | −1.17, −0.33 |
| p-Value | 0.0053* | 0.0002* | 0.0005* |

*Statistically Significant

As can be seen, TP-1 demonstrated a statistically significant and meaningful improvement in iTNSS versus Pbo-1 (pH=3.7) over the first 6, 30 and 52 weeks of the study.

The table below summarizes the results for the Quality of Life Endpoint: RQLQ (S) (full set analysis, FAS).

| | TP-1 vs. Pbo-1 (pH = 3.7) | | |
|---|---|---|---|
| | 6 weeks | 30 weeks | 52 Weeks |
| N (TP-1/Pbo-1) | 371/95 | 322/84 | 286/72 |
| Treatment Difference | −0.42 | −0.33 | −0.04 |
| 95% CI | −0.70, −0.14 | −0.60, −0.05 | −0.34, −0.26 |
| p-Value | 0.0035* | 0.0186* | 0.7902 |

*Statistically Significant

As can be seen, TP-1 demonstrated a statistically significant and meaningful improvement in RQLQ (S) versus Pbo-1 (pH=3.7) over the first 6 and 30 weeks of the study.

Example 10

Pharmacokinetics of Olopatadine in a Fixed Dose Combination of Mometasone Furoate and Olopatadine Hydrochloride Nasal Spray The pharmacokinetics of olopatadine in a fixed dose combination of mometasone furoate and olopatadine hydrochloride nasal spray was evaluated in a clinical trial. The clinical trial was a randomized, single-center, single-dose, open-label, three-period, six-sequence, cross-over study to evaluate three treatments administered as a nasal spray. The three treatments included a combination of mometasone furoate and olopatadine hydrochloride nasal spray, olopatadine hydrochloride nasal spray and PATANASE® nasal spray.

Subjects were randomized to 1 of 6 treatment sequences in a 1:1:1:1:1:1 ratio with all subjects receiving single doses of a fixed dose combination of mometasone furoate and olopatadine hydrochloride nasal spray, olopatadine hydrochloride nasal spray, and PATANASE® nasal spray. The study consisted of a screening visit, 3 single-dose treatment periods with washout periods of 7 to 14 days between dosing in each treatment period, an early withdrawal visit if applicable, and a follow-up telephone call (or visit) 1 to 7 days after completing the third treatment period.

A total of 30 subjects were randomized to 1 of 6 treatment sequences and received at least 1 dose of study drug. All 30 subjects were included in the safety analysis set and the pharmacokinetic subset. All but 2 subjects completed the study per protocol. The safety analysis set consisted of 30 subjects: 29, 29, and 30 subjects in the safety analysis set received a single dose of the fixed dose combination of mometasone furoate and olopatadine hydrochloride nasal spray, olopatadine hydrochloride nasal spray, and PATANASE® nasal spray, respectively. The pharmacokinetic subset consisted of 30 subjects: 29, 29, and 30 subjects in the pharmacokinetic subset received a single dose of the fixed dose combination of mometasone furoate and olopatadine hydrochloride nasal spray, olopatadine hydrochloride nasal spray, and PATANASE® nasal spray, respectively.

Quantifiable concentrations of olopatadine were observed until the last time point (48 hours). All 3 treatments were well tolerated. No subject died or reported a serious adverse event; and only one subject discontinued due to a treatment-emergent adverse event (mild oropharyngeal pain) in this study. Treatment-emergent adverse events and treatment-related treatment emergent adverse events were evenly distributed across the 3 treatments. All treatment-emergent adverse events were mild. There was no clinically significant effect of any of the treatments on laboratory values, vital sign measurements, or ECG parameters.

Example 11

Pharmacokinetics of Mometasone Furoate in a Fixed Dose Combination of Mometasone Furoate and Olopatadine Hydrochloride Nasal Spray The pharmacokinetics of mometasone furoate in a fixed dose combination of mometasone furoate and olopatadine hydrochloride nasal spray was evaluated in a clinical trial. The clinical trial was a randomized, single-center, single-dose, open-label, three-period, six-sequence, cross-over study to evaluate three treatments administered by nasal spray. The three treatments included a combination of mometasone furoate and olopatadine hydrochloride nasal spray, mometasone furoate nasal spray and Nasonex® nasal spray.

Subjects were randomized to 1 of 6 treatment sequences in a 1:1:1:1:1:1 ratio with all subjects receiving single doses of a fixed dose combination of mometasone furoate and olopatadine hydrochloride nasal spray, mometasone furoate nasal spray and Nasonex® nasal spray. The study consisted of a screening visit, 3 single-dose treatment periods with washout periods of 7 to 14 days between dosing in each treatment period, an early withdrawal visit if applicable, and a follow-up telephone call (or visit) 1 to 7 days after completing the third treatment period.

A total of 30 subjects were randomized to 1 of 6 treatment sequences and received at least 1 dose of study drug. All 30 subjects were included in the safety analysis set and the pharmacokinetic subset. All but 2 subjects completed the study per protocol. The safety analysis set consisted of 30 subjects: 29, 29, and 30 subjects in the safety analysis set received a single dose of the fixed dose combination of mometasone furoate and olopatadine hydrochloride nasal spray, mometasone furoate nasal spray and Nasonex® nasal spray, respectively. The pharmacokinetic subset consisted of 30 subjects: 29, 29, and 30 subjects in the pharmacokinetic subset received a single dose of the fixed dose combination of mometasone furoate and olopatadine hydrochloride nasal spray, mometasone furoate nasal spray and Nasonex® nasal spray respectively.

Quantifiable concentrations of mometasone furoate were observed until the last time point (72 hours). All 3 treatments were well tolerated. No subject died or reported a serious adverse event, or discontinued due to a treatment-emergent adverse event in this study. Treatment-emergent adverse events were evenly distributed across the 3 treatments. All treatment-emergent adverse events were mild. There was no clinically significant effect of any of the treatments on laboratory values, vital sign measurements, or ECG parameters.

| Therapy | Pharmacokinetic Parameters | | | |
|---|---|---|---|---|
| | $AUC_{(0-t)}$ | $AUC_{(0-infinity)}$ | $C_{max}$ | $T_{max}$ |
| Olopatadine in fixed dose combination of mometasone furoate and olopatadine hydrochloride, nasal spray | 70.95 ng · h/mL | 83.26 ng · h/mL | 17.27 ng/mL | 1.00 hr |
| Mometasone furoate in fixed dose combination of mometasone furoate and olopatadine hydrochloride nasal spray | 84.97 pg · h/mL | 103.77 pg · h/mL | 10.81 pg/mL | 1.00 hr |
| Relative Bioavailability of fixed dose combination of mometasone furoate and olopatadine hydrochloride nasal spray versus: | | | | |
| Patanase ® (Geometric mean ratio %) | 87.87 | 93.80 | 84.68 | — |
| Nasonex ® (Geometric mean ratio %) | 109.92 | 115.14 | 141.84 | — |
| olopatadine hydrochloride (Geometric mean ratio %) | 86.92 | 92.83 | 86.63 | — |
| mometasone furoate (Geometric mean ratio %) | 118.36 | 118.50 | 113.83 | — |

Example 12

Phase III Clinical Study of Fixed Dose Combination of Mometasone and Olopatadine Nasal Spray in Pediatric Patients This study is a double blind, randomized, parallel-group, 12-week study to evaluate the efficacy, safety, and tolerability of a fixed dose combination of mometasone furoate and olopatadine hydrochloride nasal spray compared with a placebo nasal spray in pediatric subjects (aged 2 to under 12 years) with perennial seasonal allergic rhinitis (PAR).

Study Objectives

To compare the efficacy of mometasone furoate and olopatadine hydrochloride nasal spray (administered as 1 spray per nostril twice daily) with a placebo nasal spray for treatment in pediatric subjects (aged ≥2 to <12 years) with PAR.

A secondary objective is to compare the safety and tolerability of mometasone furoate and olopatadine hydrochloride nasal spray with a placebo nasal spray over 12 weeks of study treatment.

Key Subject Selection Criteria

- Male or non-pregnant female subjects aged ≥2 to <12 years, as of the Screening Visit (Visit 1).
- Documented clinical history of PAR (≥12 months for subjects aged ≥6 to <12 years, ≥6 months for subjects aged ≥2 to <6 years preceding the Screening Visit [Visit 1]) with exacerbations (clinical evidence of active symptoms). In the judgment of the Investigator, the PAR must have been of sufficient severity to have required treatment (either continuous or intermittent) in the past and is expected to require treatment for the study duration.
- Documented positive skin prick test (wheal diameter at least 3 mm greater than negative control wheal) to at least one allergen known to induce PAR. Documentation of a positive result within 12 months prior to the Screening Visit (Visit 1) is acceptable. Positive allergen test for the subject that must be consistent with the medical history of PAR. Additionally the subject is expected to be exposed to the PAR allergen that he or she tested positive for via the skin prick test for the entire duration of the study.
- A 12-hour rTNSS value of ≥6 (out of a possible 12) for the AM assessment at the Screening Visit (Visit 1).

Study Design

A total of approximately 540 subjects (≥2 to <12 years) will be randomized in the study in a 2:1 ratio for a fixed dose combination of mometasone furoate and olopatadine hydrochloride nasal spray (360 subjects) versus placebo nasal spray (180 subjects).

The study will be 12 weeks in duration. The subject participation may extend up to 13 to 14 weeks consisting of up to 7 to 10 days of a screening/placebo run-in period and 12 weeks of treatment period with allowable window periods for the study visits. The treatment groups are provided in the table below.

Investigational Products and their Administration

| Investigational product(s) | Administration |
| --- | --- |
| Olopatadine hydrochloride + mometasone furoate (665 μg + 25 μg) nasal spray* | 1 spray per nostril, twice daily (BID) in morning and evening |
| Placebo nasal spray | Placebo - 1 spray per nostril twice daily (BID) in morning and evening |

*Each spray provides 665 μg olopatadine hydrochloride and 25 μg mometasone furoate.

Primary Endpoint:
  Change from baseline in average AM and PM subject-reported 12-hour reflective Total Nasal Symptom Score (rTNSS) over the first 4 weeks of treatment for subjects ≥6 to <12 years of age.

Secondary Endpoint(s):
  Change from baseline in average AM and PM subject-reported 12-hour instantaneous Total Nasal Symptom Score (iTNSS) over the first 4 weeks of treatment for subjects ≥6 to <12 years of age.
  Change from baseline in average AM and PM subject-reported 12-hour rTNSS over the first 4 weeks of treatment for subjects ≥2 to <12 years of age.
  Change from baseline in average AM and PM subject-reported 12-hour iTNSS over the first 4 weeks of treatment for subjects ≥2 to <12 years of age.
  Change from baseline in the overall Pediatric Rhinoconjunctivitis Quality of Life Questionnaire (PRQLQ) score at Week 4 between treatment groups.

Other Endpoint(s):
  Nasal Symptoms:
  TNSS—First 4 Weeks, Subjects Aged ≥6 to <12 Years:
    Change from baseline in AM subject-reported rTNSS over the first 4 weeks of treatment.
    Change from baseline in PM subject-reported rTNSS over the first 4 weeks of treatment.
    Change from baseline in AM subject-reported iTNSS over the first 4 weeks of treatment.
    Change from baseline in PM subject-reported iTNSS over the first 4 weeks of treatment.
    Change from baseline in subject-reported reflective individual nasal symptoms over the first 4 weeks of treatment period (AM, PM and average of AM and PM).
    Change from baseline in subject-reported instantaneous individual nasal symptoms over the first 4 weeks of treatment period (AM, PM and average of AM and PM).
    Change from baseline subject-reported rTNSS and iTNSS for each day (AM, PM and average of AM and PM).
  TNSS—First 4 Weeks, Subjects Aged ≥2 to <6 Years:
    Change from baseline in average AM and PM subject-reported 12-hour rTNSS over the first 4 weeks of treatment for subjects aged ≥2 to <6 years.
    Change from baseline in average AM and PM subject-reported 12-hour iTNSS over the first 4 weeks of treatment for subjects aged ≥2 to <6 years.
  TNSS—First 4 Weeks, Subjects Aged ≥2 to <12 Years:
    Change from baseline in average AM and PM subject-reported 12-hour rTNSS over the first 4 weeks of treatment for subjects aged ≥2 to <12 years.
    Change from baseline in average AM and PM subject-reported 12-hour iTNSS over the first 4 weeks of treatment for subjects aged ≥2 to <12 years.
  Additional Total Nasal Symptom Score (TNSS) outcomes will be assessed for the following (e.g. AM, PM, Individual symptoms):
    12 weeks, subjects aged ≥6 to <12 years.
    12 weeks, subjects aged ≥2 to <6 years.
    12 weeks, subjects aged ≥2 to <12 years.
  Physician Assessed Nasal Symptom Score (PNSS):
    Change from baseline in PNSS and physician assessed individual nasal symptoms at Weeks 4 and 12.
  Pediatric Rhinoconjuntivitis Quality of Life Questionnaire (PRQLQ):
    Individual domains of the PRQLQ at Weeks 4 and 12.

Example 13

Phase III Clinical Study of Fixed Dose Combination of Mometasone and Olopatadine Nasal Spray in Pediatric Patients This study is a double blind, randomized, parallel-group 14 day study to evaluate the efficacy, safety, and tolerability of a fixed dose combination of mometasone furoate and olopatadine hydrochloride nasal spray compared with a placebo nasal spray over 14 days in pediatric subjects (aged 6 to under 12 years) with seasonal allergic rhinitis (SAR).

Study Objectives

To compare the efficacy of mometasone furoate and olopatadine hydrochloride nasal spray (administered as 1 spray per nostril twice daily) with a placebo nasal spray for treatment in pediatric subjects (aged ≥6 to <12 years) with SAR.

A secondary objective is to compare the safety and tolerability of mometasone furoate and olopatadine hydrochloride nasal spray with a placebo nasal spray over the study period.

Key Subject Selection Criteria

Male or non-pregnant female subjects aged ≥6 to <12 years, at the Screening Visit (Visit 1).

Documented clinical history of SAR (for at least 2 years preceding the Screening Visit [Visit 1]) with exacerbations (clinical evidence of active symptoms) during the study season for the relevant seasonal allergen (tree/grass pollen). SAR must have been of sufficient severity to have required treatment (either continuous or intermittent) in the past, and in the investigator's judgment, is expected to require treatment throughout the study period.

Demonstrated sensitivity to at least 1 seasonal allergen (tree/grass pollen) known to induce SAR through a documented positive skin prick test (wheal diameter at least 5 mm greater than the negative control) to a relevant seasonal allergen. Documentation of a positive result within 12 months prior to the Screening Visit (Visit 1) is acceptable. The subject's positive allergen must be consistent with the medical history of SAR. Additionally, the subject is expected to be adequately exposed to the SAR allergen that he/she has tested positive for the entire duration of the study.

A 12-hour reflective Total Nasal Symptom Score (rTNSS) value of ≥6 (out of a possible 12) for the morning (AM) assessment at the Screening Visit (Visit 1).

Study Design

A total of approximately 450 subjects (≥6 to <12 years) will be randomized in the study in a 1:1 ratio for a fixed dose combination of mometasone furoate and olopatadine hydrochloride nasal spray (225 subjects) versus placebo nasal spray (225 subjects).

The treatment groups are provided in the table below.

Investigational Products and their Administration

| Investigational product(s) | Administration |
| --- | --- |
| Olopatadine hydrochloride + mometasone furoate (665 μg + 25 μg) nasal spray* | 1 spray per nostril, twice daily (BID) in morning and evening |
| Placebo nasal spray | Placebo - 1 spray per nostril twice daily (BID) in morning and evening |

*Each spray provides 665 μg olopatadine hydrochloride and 25 μg mometasone furoate.

The subject participation may be 22 days up to 27 days with 7 to 10 days of a screening/run-in period and 14 days of treatment period, with allowable window periods for the study visits.

Key Evaluation Criteria (Clinical Endpoints):

Primary Endpoint

Change from baseline in average AM and PM subject-reported 12-hour reflective Total Nasal Symptom Score (rTNSS) over the 14 day treatment period.

Secondary Endpoint(s):

Change from baseline in average AM and PM subject-reported 12-hour instantaneous Total Nasal Symptom Score (iTNSS) over the 14 day treatment period.

Change from baseline in the overall Pediatric Rhinoconjunctivitis Quality of Life Questionnaire (PRQLQ) score on Day 15 (Visit 4) between treatment groups.

Change from baseline in average AM and PM subject-reported 12-hour reflective Total Ocular Symptom Score (rTOSS) over the 14-day treatment period.

Other Efficacy Endpoint(s):

Nasal Symptoms

Change from baseline in AM subject-reported rTNSS over the 14-day treatment period.

Change from baseline in AM subject-reported iTNSS over the 14-day treatment period.

Change from baseline in PM subject-reported rTNSS over the 14-day treatment period.

Change from baseline in PM subject-reported iTNSS over the 14-day treatment period.

Change from baseline in subject-reported reflective individual nasal symptoms over the 14-day treatment period (AM, PM and average of AM and PM).

Change from baseline in subject-reported instantaneous individual nasal symptoms over the 14-day treatment period (AM, PM and average of AM and PM).

Change from baseline in average AM and PM subject-reported rTNSS and iTNSS for each day.

Change from baseline in AM subject-reported rTNSS and iTNSS for each day.

Change from baseline in PM subject-reported rTNSS and iTNSS for each day.

Ocular Symptoms:

Change from baseline in average AM and PM subject-reported instantaneous Total Ocular Symptom Score (iTOSS) over the 14-day treatment period.

Change from baseline in AM subject-reported rTOSS over the 14-day treatment period.

Change from baseline in AM subject-reported iTOSS over the 14-day treatment period.

Change from baseline in PM subject-reported rTOSS over the 14-day treatment period.

Change from baseline in PM subject-reported iTOSS over the 14-day treatment period.

Change from baseline in subject-reported reflective individual ocular symptoms over the 14-day treatment period (AM, PM, and average AM and PM).

Change from baseline in subject-reported instantaneous individual ocular symptoms over the 14-day treatment period (AM, PM, and average AM and PM).

Change from baseline in average of the AM and PM subject-reported rTOSS and iTOSS for each day.

Change from baseline in AM subject-reported rTOSS and iTOSS for each day.

Change from baseline in PM subject-reported rTOSS and iTOSS for each day.

Non-nasal symptoms will be assessed in a similar manner to the ocular symptoms above (as described in the Statistical Analysis Plan [SAP]).

Physician Assessed Nasal Symptom Score (PNSS):

Change from baseline in PNSS and physician assessed individual nasal symptoms at Day 15 (Visit 4).

Pediatric Rhinoconjuntivitis Quality of Life Questionnaire (PRQLQ):
  Change from baseline in individual domains of the PRQLQ at Day 15.

Although the invention herein has been described with reference to particular embodiments, it is to be understood that these embodiments are merely illustrative of the principles and application of the present invention. It is therefore to be understood that numerous modifications may be made to the illustrative embodiments and that other arrangements may be devised without departing from the spirit and scope of the present invention as described.

All publications, patents, and patent applications cited in this application are herein incorporated by reference to the same extent as if each individual publication, patent, or patent application was specifically and individually indicated to be incorporated herein by reference.

What is claimed is:

1. A dispensing device and pharmaceutical composition for nasal administration to a human, comprising:
   a container having a conically shaped internal bottom, wherein the internal bottom is angled downwardly from a side of the container toward a center, the center located along a longitudinal axis of the container, the internal bottom including a further angularly deepened well centrally located about the longitudinal axis, said well including a groove therein, the groove further deepening an internal bottom of the well, the groove extending across the longitudinal axis of the container, whereby the internal bottom of the well, at the center, is a low point of the internal bottom of the container;
   a dispenser head for dispensing the pharmaceutical composition from the container, the dispenser head comprising at least a pump, a dispensing channel, and a dispensing orifice;
   a dip tube extending along the longitudinal axis of the container, the dip tube having a proximal end communicating with the dispenser head and an open distal end extending into the well; wherein the open distal end of the dip tube extends into the groove or is located at a top of the groove; and
   a pharmaceutical composition in the container, the pharmaceutical composition comprising:
     about 0.001% w/w to about 0.075% w/w mometasone, an ester thereof, or a salt thereof in particulate form;
     about 0.5% w/w to about 0.8% w/w olopatadine or its salt in dissolved form; and
     a hydrocolloid in an amount sufficient to inhibit phase separation for at least 24 hours when stored at 25±2° C. and 60%±5% relative humidity.

2. The dispensing device and pharmaceutical composition of claim 1, wherein a dimension of the groove, further deepening the internal bottom of the well, does not affect an external bottom of the well, as the dimension is within a wall thickness of the bottom of the well.

3. The dispensing device and pharmaceutical composition of claim 1, wherein the pharmaceutical composition contains not more than 1% of total impurities when stored for up to 12 months.

4. The dispensing device and pharmaceutical composition of claim 1, wherein the dispensing device dispenses about 100 µl of the pharmaceutical composition per actuation, wherein a single actuation dispenses about 665 mcg of olopatadine and about 25 mcg or about 50 mcg of mometasone.

5. The dispensing device and pharmaceutical composition of claim 1, wherein the dispenser head is defined exteriorly by at least an end wall and a lateral wall, the end wall including the dispensing orifice; the dispensing device further including a cap releasably attachable to the dispenser head for covering at least the dispensing orifice, the cap including a sealing sleeve, extending from an interior surface of the cap, that communicates in a seal tight manner with a perimeter of the lateral wall of the dispenser head.

6. The dispensing device and pharmaceutical composition of claim 5, wherein an inner diameter of a distal end of the sealing sleeve is smaller than an exterior diameter of the lateral wall of the dispenser head, at a point of communication of the sealing sleeve with the lateral wall, to create the seal tight manner when the cap is in a closed position, whereby the distal end of the sealing sleeve is radially deformed.

7. The dispensing device and pharmaceutical composition of claim 1, wherein the pharmaceutical composition is configured to be delivered from the dispensing device to a patient suffering from allergic rhinitis to provide relief from symptoms of allergic rhinitis.

8. The dispensing device and pharmaceutical composition of claim 1, wherein the pharmaceutical composition comprises about 0.025% w/w mometasone furoate, about 0.665% w/w olopatadine hydrochloride, about 0.5% w/w carboxymethyl cellulose sodium, about 1.2% w/w mixture of microcrystalline cellulose and carboxymethyl cellulose sodium, about 0.02% w/w benzalkonium chloride, about 0.4% w/w sodium chloride, about 0.01% w/w di-sodium edetate, about 0.94% w/w sodium phosphate heptahydrate, and about 0.01% w/w polysorbate 80.

9. A dispensing device and pharmaceutical composition for nasal administration to a human, comprising:
   a container having a conically shaped internal bottom, wherein the internal bottom is angled downwardly from a side of the container toward a center, the center located along a longitudinal axis of the container, the internal bottom including a further angularly deepened well centrally located about the longitudinal axis, wherein the well of the internal bottom of the container further includes a groove therein, the groove further deepening an internal bottom of the well in a dimension greater than a wall thickness of the bottom of the well, thereby requiring modification of an external bottom of at least the well, wherein a support bead, with the groove therein, extends from at least an external bottom of the well, the support bead also extending across the longitudinal axis of the container;
   a dispenser head for dispensing the pharmaceutical composition from the container, the dispenser head comprising at least a pump, a dispensing channel, and a dispensing orifice;
   a dip tube extending along the longitudinal axis of the container, the dip tube having a proximal end communicating with the dispenser head and an open distal end extending into the well; wherein the open distal end of the dip tube extends into the groove or is located at a top of the groove; and
   a pharmaceutical composition in the container, the pharmaceutical composition comprising:
     about 0.001% w/w to about 0.075% w/w mometasone, an ester thereof, or a salt thereof in particulate form;
     about 0.5% w/w to about 0.8% w/w olopatadine or its salt in dissolved form; and
     a hydrocolloid in an amount sufficient to inhibit phase separation for at least 24 hours when stored at 25±2° C. and 60%±5% relative humidity.

10. A dispensing device and pharmaceutical composition for administration to a human, comprising:
- a container having a conically shaped internal bottom, the internal bottom being angled downwardly from a side of the container toward a center, the center located along a longitudinal axis of the container, the internal bottom including a further angularly deepened well centrally located about the longitudinal axis, the well including a groove therein, the groove further deepening an internal bottom of the well, the groove extending across the longitudinal axis of the container, whereby the internal bottom of the well, at the center, is a low point of the internal bottom of the container;
- a dispenser head for dispensing the pharmaceutical composition from the container, the dispenser head comprising at least a pump, a dispensing channel, and a dispensing orifice, the dispenser head defined exteriorly by at least an end wall and a lateral wall, the end wall including the dispensing orifice;
- a cap releasably attachable to the dispenser head for covering at least the dispensing orifice, the cap including a sealing sleeve, extending from an interior surface of the cap, that communicates in a seal tight manner with a perimeter of the lateral wall of the dispenser head;
- a dip tube extending along the longitudinal axis of the container, the dip tube having a proximal end communicating with the dispenser head and an open distal end extending into the well; wherein the open distal end of the dip tube extends into the groove or is located at a top of the groove; and
- a pharmaceutical composition of single phase suspension in the container, the pharmaceutical composition comprising:
  - about 0.001% w/w to about 0.075% w/w mometasone, an ester thereof, or a salt thereof in particulate form;
  - about 0.5% w/w to about 0.8% w/w olopatadine or its salt in dissolved form; and
  - a hydrocolloid system in an amount sufficient to inhibit phase separation for at least 24 hours when stored at 25±2° C. and 60%±5% relative humidity.

11. The dispensing device and pharmaceutical composition of claim 10, wherein the sealing sleeve extends from a top inside wall of the cap.

12. The dispensing device and pharmaceutical composition of claim 11, wherein an inner diameter of a distal end of the sealing sleeve is smaller than an exterior diameter of the lateral wall of the dispenser head, at a point of communication of the sealing sleeve with the lateral wall, to create the seal tight manner when the cap is in a closed position, whereby the distal end of the sealing sleeve is radially deformed.

13. The dispensing device and pharmaceutical composition of claim 11, wherein the sealing sleeve has a wall thickness that decreases as the sealing sleeve extends away from the top inside wall of the cap.

14. The dispensing device and pharmaceutical composition of claim 10, wherein the cap includes, on an interior thereof, one or more protruding tabs that snap fit against the lateral wall of the dispenser head to hold the cap securely on the dispenser head in a closed position.

15. The dispensing device and pharmaceutical composition of claim 10, wherein the pharmaceutical composition has a pH of about 3.3-4.1, and an osmolality in the range of about 200 mOsm/kg to about 400 mOsm/kg.

16. The dispensing device and pharmaceutical composition of claim 10, wherein the dispensing device dispenses about 100 µl of the pharmaceutical composition per actuation, wherein a single actuation dispenses about 665 mcg of olopatadine hydrochloride and about 25 mcg or about 50 mcg of mometasone furoate.

\* \* \* \* \*